(12) United States Patent
Nomura et al.

(10) Patent No.: US 6,506,797 B1
(45) Date of Patent: Jan. 14, 2003

(54) SUBSTITUTED PHENYLPROPIONIC ACID DERIVATIVES AS AGONISTS TO HUMAN PEROXISOME PROLIFERATOR-ACTIVATED RECEPTOR (PPAR) α

(75) Inventors: Masahiro Nomura, Nogi-machi (JP); Yukie Takahashi, Nogi-machi (JP); Takahiro Tanase, Nogi-machi (JP); Hiroyuki Miyachi, Kazo (JP); Masaki Tsunoda, Kasukabe (JP); Tomohiro Ide, Koga (JP); Koji Murakami, Oyama (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 286 days.

(21) Appl. No.: 10/009,175

(22) PCT Filed: Jun. 8, 2000

(86) PCT No.: PCT/JP00/03707

§ 371 (c)(1),
(2), (4) Date: Dec. 10, 2001

(87) PCT Pub. No.: WO00/75103

PCT Pub. Date: Dec. 14, 2000

(30) Foreign Application Priority Data

Jun. 9, 1999 (JP) .......................................... 11-162235
May 29, 2000 (JP) ....................................... 2000-157600

(51) Int. Cl.⁷ .......................... A01N 37/12; C07C 63/00
(52) U.S. Cl. ..................... 514/562; 562/405; 562/442; 562/443
(58) Field of Search ................................ 562/405, 442, 562/443; 514/562

(56) References Cited

U.S. PATENT DOCUMENTS 6,028,109 A  2/2000  Wilson

FOREIGN PATENT DOCUMENTS

| CN | 1212622 | 3/1999 |
| JP | 2000-503643 | 3/2000 |
| WO | 97/25042 | 7/1997 |
| WO | WO 97/25042 | * 7/1997 |
| WO | WO 97/36579 | * 8/1997 |
| WO | WO 97/36579 | 10/1997 |
| WO | 97/36579 | 10/1997 |

* cited by examiner

Primary Examiner—Alan L. Rotman
Assistant Examiner—Héctor M. Reyes
(74) Attorney, Agent, or Firm—Oblon, Spivak, McClelland, Maier & Neustadt, P.C.

(57) ABSTRACT

The invention provides novel substituted phenylpropanoic acid derivatives that activate by binding to receptor as ligands of human peroxisome preliferant-activated receptor α (PPARα), and exhibit potent decreasing action on lipids in blood (cholesterol and triglyceride).

It relates to a substituted phenylpropanoic acid derivatives represented by a general formula (1),

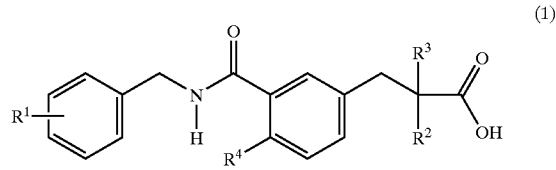

(1)

their pharmaceutically acceptable salts and their hydrates, and processes for preparing them.

47 Claims, No Drawings

SUBSTITUTED PHENYLPROPIONIC ACID DERIVATIVES AS AGONISTS TO HUMAN PEROXISOME PROLIFERATOR-ACTIVATED RECEPTOR (PPAR) α

TECHNICAL FIELD

The present invention relates to substituted phenylpropanoic acid derivatives, effective for the therapy of abnormality of lipidmetabolism as agonists of human peroxisome proliferant-activated receptor (abbreviated as PPAR), in particular, as agonists for human PPARα isoform, their addition salts and their hydrates, processes for preparing them, and medicinal compositions containing these compounds.

BACKGROUND TECHNOLOGIES

The peroxisome proliferant-activated receptor (PPAR)'s are a ligand-dependent transcription factors that belong to nuclear receptor superfamily, such as steroid receptor, retinoid receptor, thyroid receptor, etc. Three isoforms (α type, β (or δ) type and γ type) with different histological distribution have been identified hitherto in human and various animal species (Proc. Natl. Acad. Sci., 1992, 89, 4653). Thereamong, the PPARα is distributed in the liver, kidney, etc., with high catabolic capacity for fatty acids and, in particular high expression is recognized in the liver, (Endocrinology, 1995, 137, 354), positively or negatively controlling the expressions of genes relevant to the metabolism and the intracellular transport of fatty acids (e.g. acyl CoA synthetic enzyme, fatty acid-binding protein and lipoprotein lipase) and apolipoprotein (AI, AII, CIII) genes relevant to the metabolisms of cholesterol and neutral lipid. The PPARβ is expressed ubiquitously in the tissues or organisms, including nerve cells. At present, the physiological significance of PPARβ is unclear. The PPARγ is highly expressed in the adipocytes and involved the differentiation of adipocytes (J. Lipid Res., 1996, 37, 907). In this way, each isoform of PPAR play specific function in the particular organs and tissues.

Moreover, it is reported that a knock-out mouse of PPARα exhibits hypertriglyceridemia with ageing and becomes obesity mainly by increasing the white adipose tissues (J. Biol. Chem., 1998, 273, 29577), hence the relevance between activation of PPARα and decreasing action of lipids (cholesterol and triglyceride) in blood is suggested strongly.

On the other hand, fibrates and statins are widely used so far as the therapeutic drugs for hyperlipidemia. However, the fibrates have only weak decreasing effect of cholesterol, while the statins have weak decreasing effect of free fatty acids and triglycerides. Moreover, with respect to the fibrates, various adverse effects such as gastrointestinal injury, anthema, headache, hepatic disorder, renal disorder and biliary calculus are reported. The reason is considered to be due to that the fibrates exhibit extensive pharmacological function, hence the development of a therapeutic drug for hyperlipidemia with specific mechanism is desired.

When considering the present situation of such conventional therapeutic drugs for hyperlipidemia, and the role on the adjusting mechanism of lipidmetabolism and the connection to the pathology of hyperlipidemia of transcription factor called PPARα, which has become clear until now, if a compound that binds directly to as a ligand of PPARα, in particular, human PPARα and is capable of activating human PPARα could be created, the medicinal use thereof would be expected as a compound that exhibits the decreasing effect of lipids (both of cholesterol and triglyceride) in blood due to very specific mechanism.

Prior arts

For compounds having an affinity to PPARα as ligands of PPARα, eicosanoids in HETE (hydroxyeicosatetraenoic acid) group produced via oxidation with cytochrome P-450, in particular, 8-HETE, 8-HEPE, etc. are reported in addition to $LTB_4$ being a metabolite of arachidonic acid (Proc. Natl. Acad. Sci., 1997, 94, 312). However, these endogenous unsaturated fatty acid derivatives are unstable metabolically and chemically and cannot be offered as medicinal drugs.

On the other hand, as compounds with similar structure to the inventive substituted phenylpropanoic acid derivatives, a group of compounds shown below, etc. are reported.

As compounds with glucose-lowering action, in International Publication Number WO98/28254 (Nippon Chemiphar Co., Ltd.), compounds represented by a general formula (A)

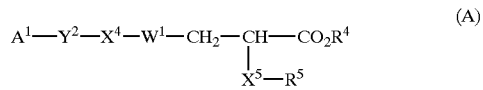

(A)

(wherein $A^1$ denotes aryl group which may have substituent or hetero-cycle group, $Y^2$ denotes alkylene chain with carbon atoms of 1 to 5, $X^4$ denotes bond hand, oxygen atom or sulfur atom, $W^1$ denotes naphthalene ring which may have substituent, quinoline ring, indole ring, benzisoxazole ring or benzo[b]thiophene ring, $R^4$ denotes hydrogen atom or alkyl group with carbon atoms of 1 to 8, $X^5$ denotes oxygen atom or sulfur atom, and $R^5$ denotes alkyl group with carbon atoms of 1 to 8 which may have substituent, aralkyl group or aryl group), are reported. These compounds however have different structure from that of the inventive compounds in that carbonyl group or amide group is not contained in $Y^2$ and $X^4$ being connecting portions and that $W^1$ to bind to 3-position of propanoic acid is heterocycle, and it is also not described that these compounds have the binding activity to human PPARα and the transcription-activating function.

As propanoic acid derivatives with glucose-lowering action and lipid-decreasing effect, in International Publication Number WO98/07699 (Japan Tobacco Inc.), compounds represented by a general formula (B)

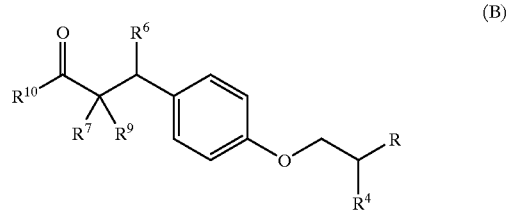

(B)

(wherein R denotes a substituent represented by $D_1$ or $D_2$, $R^1$ denotes aromatic ring, cycloalkyl group or heteroaromatic ring, $R^5$ denotes alkyl group, $R^4$ denotes hydrogen atom or alkyl group, $R^6$ denotes hydrogen atom or it may be connected to $R^9$ to form double bond, $R^7$ denotes carboxyl group, acyl group, alkoxycarbonyl group which may have substituent, alkyl group, aryloxycarbonyl group, aralkyloxycarbonyl group, carbamoyl group, $NHR^8$ group or $OR^8$ group, $R^8$ denotes acyl group which may have substituent or alkoxycarbonyl group, $R^9$ denotes hydrogen atom, alkyl group or alkoxycarbonyl group, and $R^{10}$ denotes hydrogen atom, amino group, alkoxy group, alkyl group, aryloxy group or aralkyloxy group), are reported. However, these compounds also have different structure from that of the inventive compounds in that substituents on benzene ring are of disubstituted form at 1-position and 4-position, and it is also not described that these compounds have the binding activity to human PPARα and the transcription-activating function.

As carboxylic acid derivatives with agonistic effect on leukotriene receptor, in Jpn. Kokai Tokkyo Koho JP 63-91354 (Yamanouchi Pharmaceutical Co., Ltd.), compounds represented by a general formula (C)

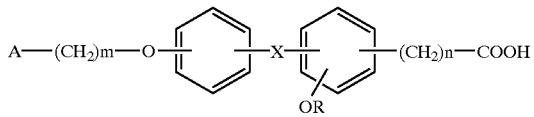

(C)

(wherein A denotes hydrogen atom or phenyl group, m denotes integer of 3 to 10, n denotes integer of 1 to 6, X denotes CONH group or NHCO group, and R denotes carboxy lower alkyl group or carboxy lower alkylcarbamoyl group (however, when A is phenyl group, R is carboxy lower alkylcarbamoyl lower alkyl group)), are reported. Among these compounds, however, propanoic acid derivatives have no substituent at 2-position and carbonyl groups exist in all of R group portions, hence the structure differs from that of the inventive compounds, and it is also not described that these compounds have the binding activity to human PPARα and the transcription-activating function.

As carboxylic acid derivatives with antagonism against fibrinogen receptor, in U.S. Pat. No. 5,227,490 (Merck & Co.,Inc.), compounds represented by a general formula (D)

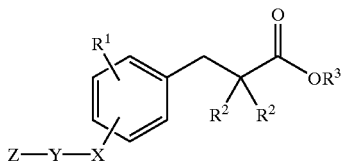

(D)

(wherein $R^1$ denotes hydrogen atom, $C_{1-6}$ alkyl group, aryl $C_{4-10}$ alkyl group, aryl group, carboxyl group, $C_{1-6}$ alkoxy group, carboxy $C_{0-6}$ alkyl group, carboxy $C_{0-6}$ alkoxy group, hydroxy $C_{1-6}$ alkyl group, $C_{1-4}$ alkylsulfonyl $C_{0-6}$ alkyl group, $C_{0-4}$ alkylamino $C_{0-6}$ alkyl group, aryl $C_{0-10}$ alkylamino $C_{0-6}$ alkyl group, $C_{2-10}$ acylamino $C_{0-6}$ alkyl group, $C_{1-4}$ carboalkoxy $C_{0-6}$ alkyl group or halogen atom, $R^2$s denote identically or differently hydrogen atoms, halogen atoms, hydroxyl groups, $C_{1-6}$ alkoxy groups, aryl $C_{0-4}$ alkyl groups, aryl $C_{0-6}$ alkoxy groups or $C_{1-6}$ alkyl groups which may have substituent, $R^3$ denotes hydrogen atom, $C_{1-6}$ alkyl group or aryl $C_{1-10}$ alkyl group, X denotes oxygen atom, sulfur atom, SO group, $SO_2$ group, CO group, $NR^4CO$ group, $CONR^4$ group, $CH_2$ group, CH=CH group or $NR^4CS$ group, Y denotes $C_{1-10}$ alkyl group which is unsubstituted or which may have substituent, $C_{4-8}$ cycloalkyl group, aryl group, $C_{0-3}$ alkyl-aryl $C_{0-3}$ alkyl group, $C_{0-3}$ alkylaryl $C_{0-3}$ alkylcarbonyl group, $C_{0-3}$ alkylaryl $C_{0-3}$ alkylcarboxyamide group, $C_{0-3}$ alkylaryloxy $C_{0-3}$ alkyl group, CONH group, NHCO group or $(CH_2)mQ-(CH_2)n$ (however, Q denotes $C_{3-8}$ membered heterocycle containing 1 to 3 kinds of heteroatoms selected from oxygen and sulfur, and m and n denote 0 to 4), and Z denotes $NR^4R^5$ group (however, $R^4$ and $R^5$ denote identically or differently hydrogen atoms, $C_{1-6}$ alkyl groups, aryl $C_{1-10}$ alkyl groups in which alkyl group is unsubstituted or may be substituted with $C_{1-4}$ alkoxy group, carboxy $C_{0-6}$ alkyl group, hydroxyl group, halogen atom, or 4–9 membered monocyclic or bicyclic ring containing 1 to 3 heteroatoms selected from nitrogen, oxygen and sulfur) or guanidino group which may have substituent), are reported. However, from the fact that these compounds are amino acid derivatives inevitably containing amino group which may have substituents in all of Z group portions, the structure is different from that of the inventive compounds, and it is also not described that these compounds have the binding activity to human PPARα and the transcription-activating function.

With respect to patents that report the agonistic effect on PPARα, compounds represented by a general formula (E)

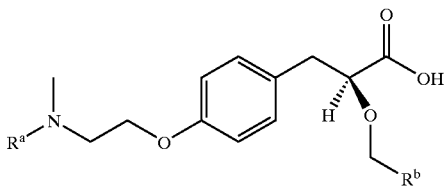

(E)

(wherein $R^a$ denotes 2-benzoxazolyl group or 2-pyridyl group, and $R^b$ denotes methoxymethyl group or trifluoromethyl group), are reported in International Publication Number WO97/25042 (SmithKline Beecham plc.) as compounds with working functions on PPARα and PPARγ. However, the structure of these compounds is different from that of the inventive compounds in that substituents on benzene ring are of disubstituted derivatives at 1-position and 2-position, and further it is not described that they have the binding activity to human PPARα and the transcription-activating function.

As compounds with agonistic effect on PPARα, in International Publication Number WO97/36579 (Glaxo Welcome Corp.), compounds represented by a general formula (F)

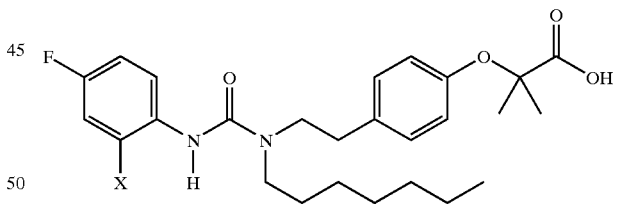

(F)

(wherein X denotes hydrogen atom or fluorine atom), are reported. However, the structure is different from that of the inventive compounds in that these compounds are phenoxyacetic acid derivatives and the position relationship of substituents on benzene ring is of disubstituted form at 1-position and 4-position. Also, the transcription-activating function of PPARα is never satisfied in strength.

SUBJECTS TO BE SOLVED BY THE INVENTION

The hyperlipidemia is a risk factor of arteriosclerosis and, from a viewpoint of the prevention of arteriosclerotic diseases, in particular, coronary arteriosclerosis, the development of a therapeutic drug for hyperlipidemia with effectiveness and high safety is desired clinically.

DISCLOSURES OF THE INVENTION

As a result of diligent studies paying an attention to such specific role on the lipidmetabolism of human PPARα, aiming at the creation of structurally novel drug with effectiveness and high safety as a therapeutic drug for hyperlipidemia, the inventors have found that novel substituted phenylpropanoic acid derivatives represented by a following general formula (1) have excellent binding activity to human PPARα and transcription-activating function and exhibit the lipid-decreasing effect, leading to the completion of the invention. Namely, the invention relates to substituted phenylpropanoic acid derivatives represented by a general formula (1)

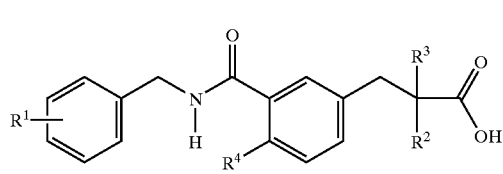

(1)

[wherein $R^1$ denotes a lower alkyl group with carbon atoms of 1 to 4, lower alkoxy group with carbon atoms of 1 to 3, trifluoromethyl group, trifluoromethoxy group, phenyl group which is unsubstituted or may have substituents, phenoxy group which is unsubstituted or may have substituents or benzyloxy group which is unsubstituted or may have substituents, $R^2$ denotes a lower alkyl group with carbon atoms of 1 to 4, 2,2,2-trifluoroethyl group, lower alkoxy group with carbon atoms of 1 to 3, phenoxy group, lower alkylthio group with carbon atoms of 1 to 3, phenylthio group or benzylthio group, $R^3$ de-notes a hydrogen atom or lower alkyl group with carbon atoms of 1 to 4 in the case of $R^2$ being lower alkyl group with carbon atoms of 1 to 4 or 2,2,2-trifluoroethyl group, and it denotes a hydrogen atom in the case of $R^2$ being lower alkoxy group with carbon atoms of 1 to 3, phenoxy group, lower alkylthio group with carbon atoms of 1 to 3, phenylthio group or benzylthio group, and $R^4$ denotes a lower alkoxy group with carbon atoms of 1 to 3], their pharmaceutically acceptable salts and their hydrates.

The salts of the compounds represented by the general formula (1) in the invention are of common use and metal salts, for example, alkali metal salts (e.g. sodium salt, potassium salt, lithium salt, etc.), alkaline earth metal salts (e.g. calcium salt, magnesium salt, etc.), aluminum salt, and other pharmaceutically acceptable salts are mentioned.

Moreover, the compounds represented by the general formula (1) in the invention sometimes include optical isomers based on the propanoic acid portion. Such isomers and their mixtures are all included in the scope of the invention.

The enantiomers can be prepared through stereoselective synthetic process. Moreover, they can also be prepared by separating diastereomeric ester derivatives or oxazolidinone derivatives obtainable by reacting with optically active alcohol derivatives or optically active oxazolidinone derivatives by a technique of fractional crystallization or chromatography, followed by hydrolysis. Furthermore, they can also be prepared by a technique of chromatography that uses chiral support.

In the general formula (1) of the invention, for "lower alkyl group with carbon atoms of 1 to 4", straight chain or branched ones with carbon atoms of 1 to 4 such as methyl, ethyl, propyl, isopropyl and butyl are mentioned.

For "lower alkoxy group with carbon atoms of 1 to 3", straight chain or branched ones with carbon atoms of 1 to 3 such as methoxy, ethoxy, isopropoxy and propoxy are mentioned.

For "halogen atoms", fluorine atom, chlorine atom, bromine atom and iodine atom are mentioned.

For "lower alkylthio group with carbon atoms of 1 to 3", straight chain or branched ones with carbon atoms of 1 to 3 such as methylthio, ethylthio and propylthio are mentioned.

For substituents acceptable in "phenyl group which is unsubstituted or may have substituents, phenoxy group which is unsubstituted or may have substituents or benzyloxy group which is unsubstituted or may have substituents", lower alkyl group with carbon atoms of 1 to 4, lower alkoxy group with carbon atoms of 1 to 3, halogen atom or trifluoromethyl group are mentioned.

The compounds of the invention can be prepared, for example, through following processes (Scheme 1).

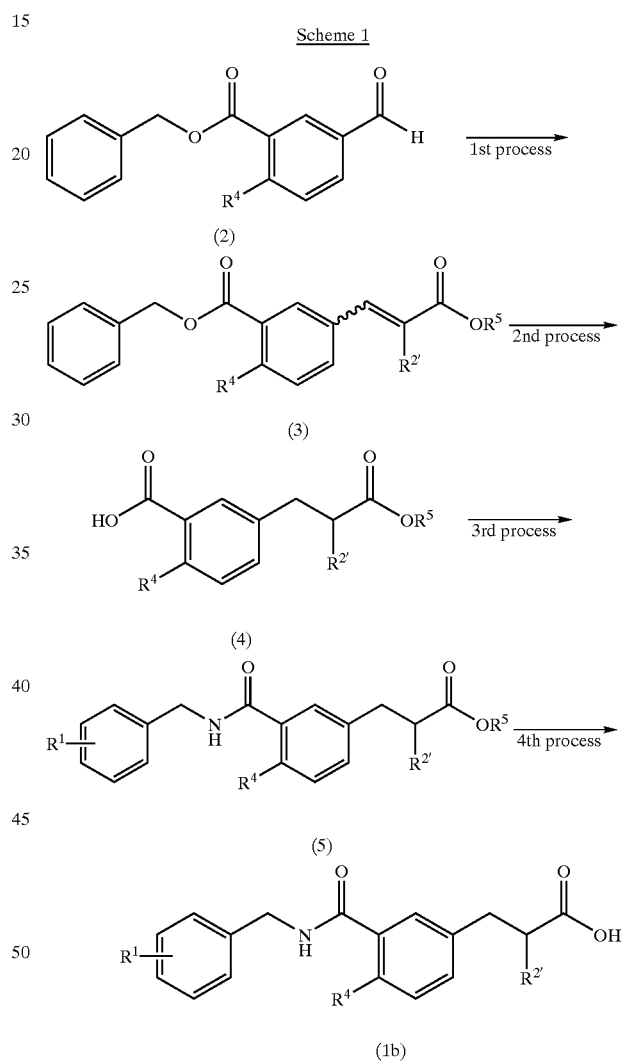

Namely, compounds represented by a general formula (1b)

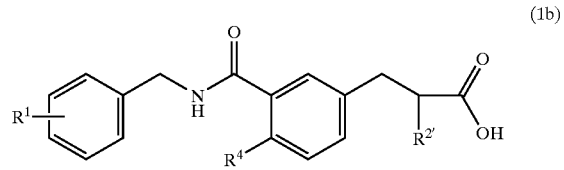

(1b)

[wherein $R^1$ denotes a lower alkyl group with carbon atoms of 1 to 4, lower alkoxy group with carbon atoms of 1 to 3, trifluoromethyl group, trifluoromethoxy group, phenyl group which is unsubstituted or may have substituents, phenoxy group which is unsubstituted or may have substituents or benzyloxy group which is unsubstituted or may have substituents, $R^{2'}$ denotes a lower alkyl group with carbon atoms of 1 to 4, lower alkoxy group with carbon atoms of 1 to 3 or phenoxy group, and $R^4$ denotes a lower alkoxy group with carbon atoms of 1 to 3], can be prepared by reacting (Wittig reaction or Horner-Emmons reaction; first process) compounds represented by a general formula (2)

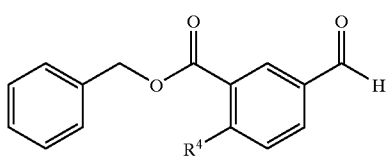

(2)

[wherein $R^4$ is as described above], and by a general formula (6)

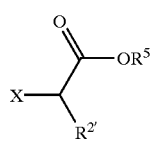

(6)

[wherein $R^{2'}$ is as described above, $R^5$ is a lower alkyl group with carbon atoms of 1 to 4, and X denotes $PPh_3$ group or $PO(OC_2H_5)_2$ group], in the presence of base, to synthesize compounds represented by a general formula (3)

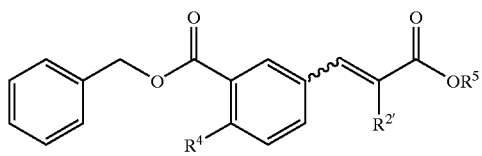

(3)

[wherein $R^{2'}$, $R^4$ and $R^5$ are as described above], by reducing and hydrogenolysis (second process) of these compounds, to obtain compounds represented by a general formula (4)

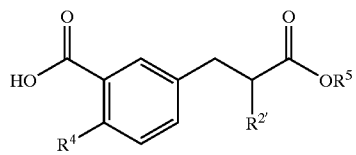

(4)

[wherein $R^{2'}$, $R^4$ and $R^5$ are as described above], by reacting (third process) these compounds with compounds represented by a general formula (7)

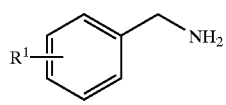

(7)

[wherein $R^1$ is as described above], to obtain compounds represented by a general formula (5)

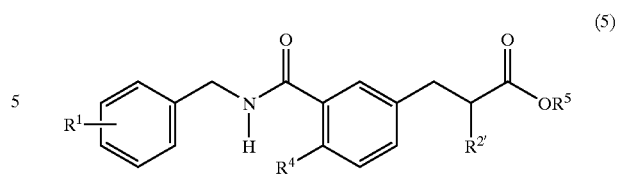

(5)

[wherein $R^1$, $R^{2'}$, $R^4$ and $R^5$ are as described above], and by hydrolizing (fourth process) $COOR^5$ position of these compounds.

In the Wittig reaction or Horner-Emmons reaction of the first process, as the base, for example, alkali metal hydride such as sodium hydride, organometallic compound such as butyl lithium, metal amide such as lithium diisopropylamide, or metal alkoxides such as sodium methoxide or potassium t-butoxide can be used in a solvent such as tetrahydrofuran, toluene, dioxane or N,N-dimethylformamide. The reaction can be performed at a reaction temperature of $-20°$ C. to 150° C., preferably 0° C. to 50° C.

The reduction being the second process can be performed at a hydrogen pressure of 98.1 kPa to 491 kPa in a solvent such as ethanol, methanol, tetrahydrofuran, ethyl acetate or N,N-dimethyl-formamide in the presence of metallic catalyst such as palladium on activated carbon, platinum on activated carbon, platinum oxide or rhodium on alumina. The reaction can be performed at a reaction temperature of 0° C. to 100° C., preferably room temperature to 80° C.

The condensation of the third process can be performed by leaving carboxyl group as it is or converting it to reactive derivatives.

As the "reactive derivative groups of carboxyl group", acid chloride, acid bromide, acid anhydride, carbonylimidazole or the like is mentioned. In the case of the reaction using reactive derivatives, the reaction can be performed in a solvent such as dioxane or N,N-dimethylformamide in the presence or absence of, for example, alkali metal hydride such as sodium hydride, alkali metal hydroxide such as sodium hydroxide, alkali metal carbonate such as potassium carbonate, or organic base such as pyridine or triethylamine as a base.

In the case of the condensation by using leaving carboxylic acid form as it is, the reaction can be performed in a solvent such as methylene chloride, chloroform, dioxane or N,N-dimethylformamide in the presence of condensing agent in the presence or absence of base, and further in the presence or absence of additive.

As the condensing agent, for example, dicyclohexylcarbodiimide, 1-[3-(dimethylamino)propyl]-3-ethylcarbodiimide hydrochloride, diethyl cyanophosphate, diphenylphosphoric azide, carbonyldiimidazole or the like can be mentioned. As the base, for example, alkali metal hydroxide such as sodium hydroxide, alkali metal carbonate such as potassium carbonate, or organic base such as pyridine or triethylamine can be mentioned. As the additive, N-hydroxybenzotriazole, N-hydroxysuccinimide, 3,4-dihydro-3-hydroxy-4-oxo-1,2,3-benzotriazine or the like can be mentioned. The reaction can be performed at a reaction temperature of $-20°$ C. to 100° C., preferably 0° C. to 50° C.

The hydrolysis of the fourth process can be performed under alkaline condition. For the alkaline condition, lithium hydroxide, sodium hydroxide, potassium hydroxide or the like is used. The reaction can be performed at a reaction temperature of 0° C. to 80° C., preferably room temperature to 60° C.

Moreover, compounds represented by the general formula (1b) can also be synthesized through following processes (Scheme 2).

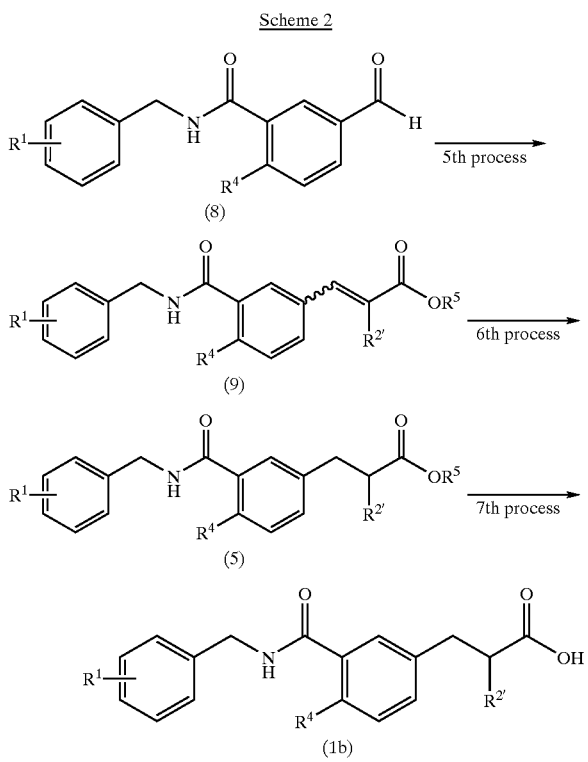

Namely, compounds represented by the general formula (1b) [wherein $R^1$, $R^{2'}$ and $R^4$ are as described above], can be prepared by reacting (Wittig reaction or Horner-Emmons reaction; fifth process) compounds represented by a general formula (8)

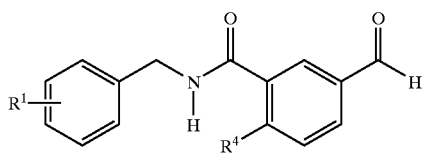

[wherein $R^1$ and $R^4$ are as described above], with compounds represented by the general formula (6)

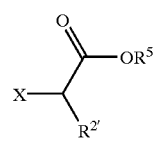

[wherein $R^{2'}$, $R^5$ and X are as described above], in the presence of base, to synthesize compounds represented by a general formula (9)

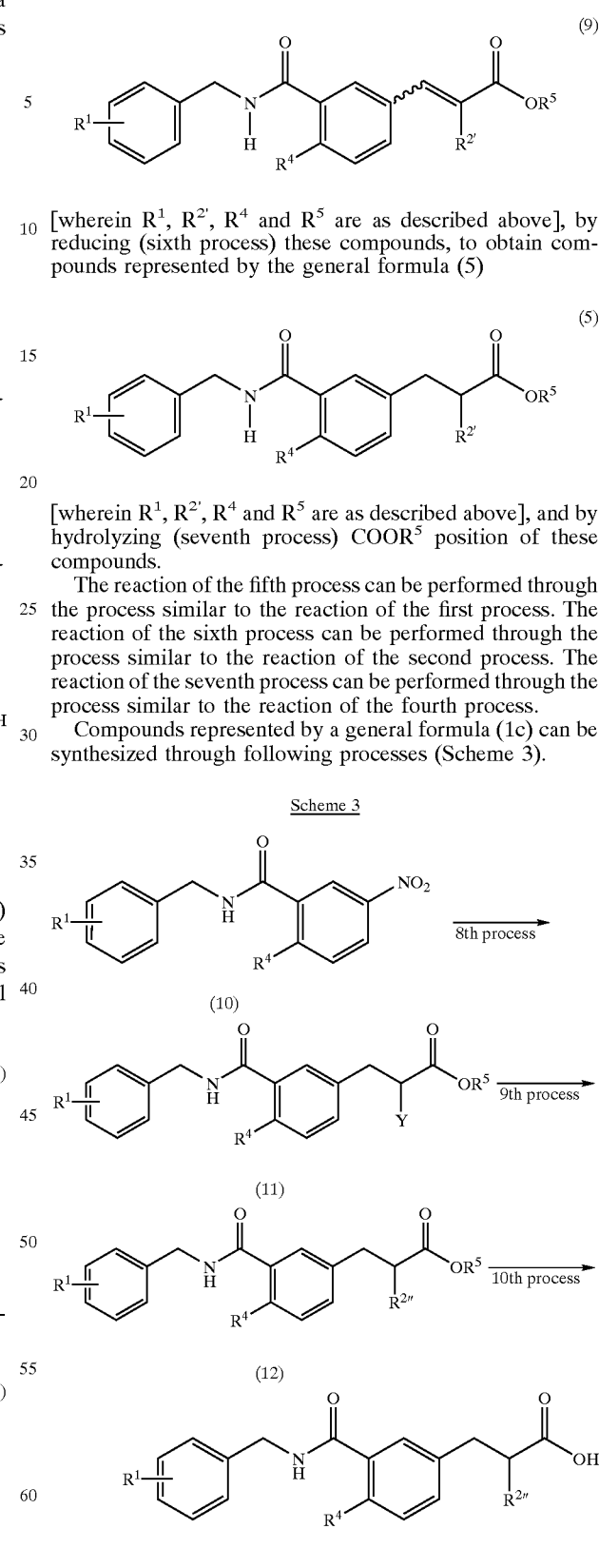

[wherein $R^1$, $R^{2'}$, $R^4$ and $R^5$ are as described above], by reducing (sixth process) these compounds, to obtain compounds represented by the general formula (5)

[wherein $R^1$, $R^{2'}$, $R^4$ and $R^5$ are as described above], and by hydrolyzing (seventh process) $COOR^5$ position of these compounds.

The reaction of the fifth process can be performed through the process similar to the reaction of the first process. The reaction of the sixth process can be performed through the process similar to the reaction of the second process. The reaction of the seventh process can be performed through the process similar to the reaction of the fourth process.

Compounds represented by a general formula (1c) can be synthesized through following processes (Scheme 3).

Namely, compounds represented by the general formula (1c)

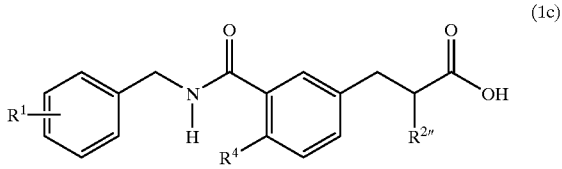

(1c)

[wherein $R^1$ denotes a lower alkyl group with carbon atoms of 1 to 4, lower alkoxy group with carbon atoms of 1 to 3, trifluoromethyl group, trifluoromethoxy group, phenyl group which is unsubstituted or may have substituents, phenoxy group which is unsubstituted or may have substituents or benzyloxy group which is unsubstituted or may have substituents, $R^{2''}$ denotes a lower alkylthio group with carbon atoms of 1 to 3, phenylthio group or benzylthio group, and $R^4$ denotes a lower alkoxy group with carbon atoms of 1 to 3], can be prepared by reducing (reduction reaction) nitro group of compounds represented by a general formula (10)

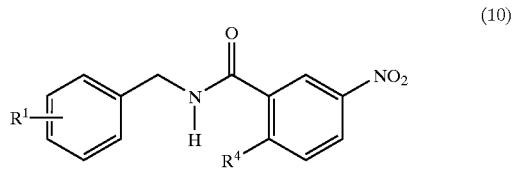

(10)

[wherein $R^1$ and $R^4$ are as described above], and then conducting Meerwein arylation reaction (eighth process), to obtain compounds represented by a general formula (11)

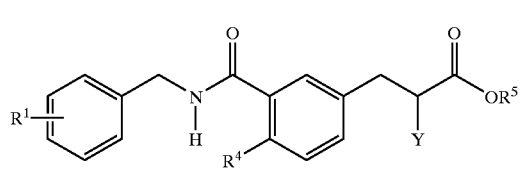

(11)

[wherein $R^1$ and $R^4$ are as described above, $R^5$ is a lower alkyl group with carbon atoms of 1 to 4, and Y denotes a halogen atom], by reacting (ninth process) these compounds with compounds represented by a general formula (13)

(13)

[wherein $R^{2''}$ is as described above], in the presence of base, to obtain compounds represented by a general formula (12)

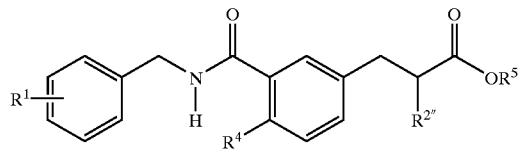

(12)

[wherein $R^1$, $R^{2''}$, $R^4$ and $R^5$ are as described above], and by hydrolyzing (tenth process) $COOR^5$ portion [$R^5$ is as described above] of these compounds.

The reaction of the eighth process can be performed first at a hydrogen pressure of 98.1 kPa to 491 kPa in a solvent such as ethanol, methanol, tetrahydrofuran, ethyl acetate or N,N-dimethylformamide in the presence of metallic catalyst such as palladium on activated carbon, platinum on activated carbon, platinum oxide or rhodium on alumina. The reaction can be performed at a reaction temperature of 0° C. to 100° C., preferably room temperature to 80° C. Next Meerwein arylation reaction can be performed by reacting sodium nitrite in aqueous solution of hydrogen halide such as hydrochloric acid or hydrobromic acid to synthesize diazonium salt, and then by adding acrylic ester such as methyl acrylate or ethyl acrylate and cuprous salt such as copper oxide (I). The synthesis of diazonium salt can be performed at a reaction temperature of −40° C. to 0° C., preferably −20° C. to −5° C. Next reaction with acrylic ester can be performed at 0° C. to 50° C., preferably room temperature to 40° C.

The reaction of the ninth process can be performed in a solvent such as ethanol, methanol or N,N-dimethylformamide, using, for example, alkali metal hydride such as sodium hydride, alkali metal hydroxide such as sodium hydroxide, alkali metal carbonate such as potassium carbonate, or the like as a base. The reaction can be performed at a reaction temperature of room temperature to 180° C., preferably at reflux temperature of the solvent.

The reaction of the tenth process can be performed through the process similar to the reaction of the fourth process.

Compounds represented by a general formula (1d) can be synthesized through following processes (Scheme 4).

Scheme 4

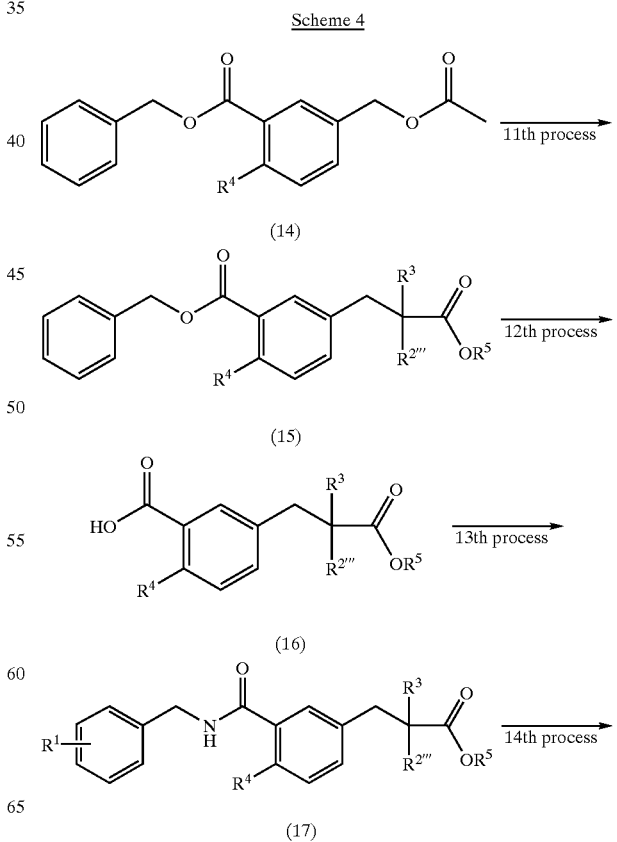

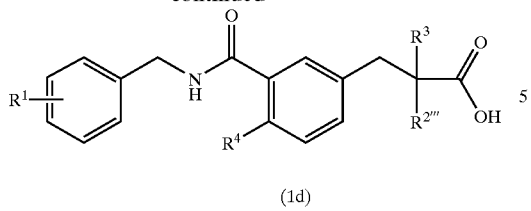

(1d)

Namely, compounds represented by the general formula (1d)

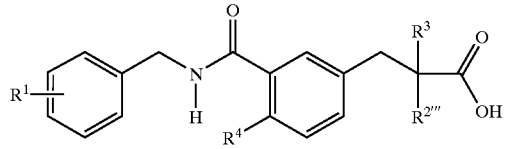

(1d)

[wherein $R^1$ denotes a lower alkyl group with carbon atoms of 1 to 4, lower alkoxy group with carbon atoms of 1 to 3, trifluoromethyl group, trifluoromethoxy group, phenyl group which is unsubstituted or may have substituents, phenoxy group which is unsubstituted or may have substituents or benzyloxy group which is unsubstituted or may have substituents, $R^{2'''}$ denotes a lower alkyl group with carbon atoms of 1 to 4 or 2,2,2-trifluoroethyl group, $R^3$ denotes a hydrogen atom or lower alkyl group with carbon atoms of 1 to 4, and $R^4$ denotes a lower alkoxy group with carbon atoms of 1 to 3], can be prepared by reacting (Tetrahedron Letters, 1997, 38, 2645; eleventh process) compounds represented by a general formula (14)

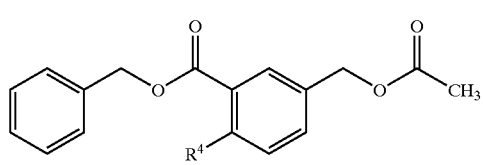

(14)

[wherein $R^4$ is as described above], with compounds represented by a general formula (22)

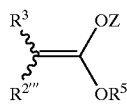

(22)

[wherein $R^{2'''}$ and $R^3$ are as described above, $R^5$ is a lower alkyl group with carbon atoms of 1 to 4, and Z denotes a trimethylsilyl group or t-butyldimethylsilyl group], in the presence of a catalytic amount of Lewis acid, to synthesize compounds represented by a general formula (15)

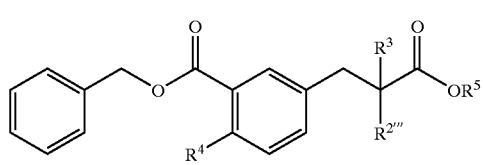

(15)

[wherein $R^{2'''}$, $R^3$, $R^4$ and $R^5$ are as described above], by hydrogenolysis (twelfth process) these compounds, to obtain compounds represented by a general formula (16)

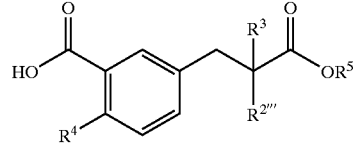

(16)

[wherein $R^{2'''}$, $R^3$, $R^4$ and $R^5$ are as described above], by reacting (thirteenth process) these compounds with compounds represented by the general formula (7)

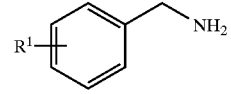

(7)

[wherein $R^1$ is as described above], to obtain compounds represented by a general formula (17)

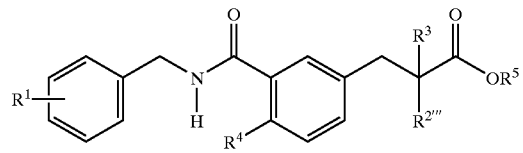

(17)

[wherein $R^{2'''}$, $R^3$, $R^4$ and $R^5$ are as described above], and by hydrolyzing (fourteenth process) $COOR^5$ position of these compounds.

The reaction of the eleventh process can be performed in a solvent such as dichloromethane, tetrahydrofuran, toluene or dioxane, using, for example, magnesium perchlorate, magnesium bistrifluoromethanesulfonylimide, titanium tetrachloride or the like as a Lewis acid. The reaction can be performed at a reaction temperature of −20° C. to 80° C., preferably 0° C. to 50° C.

The reaction of the twelfth process can be performed through the process similar to the reaction of the second process. The reaction of the thirteenth process can be performed through the process similar to the reaction of the third process. The reaction of the fourteenth process can be performed through the process similar to the reaction of the fourth process.

Moreover, optically active compounds of the general formula (1a) can be prepared, for example, through following processes (Scheme 5).

Scheme 5

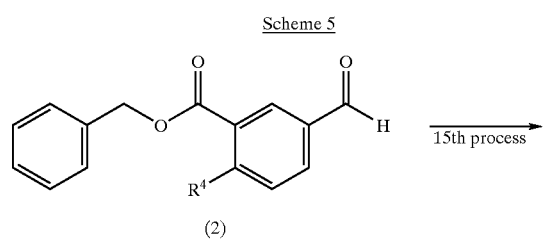

(2)

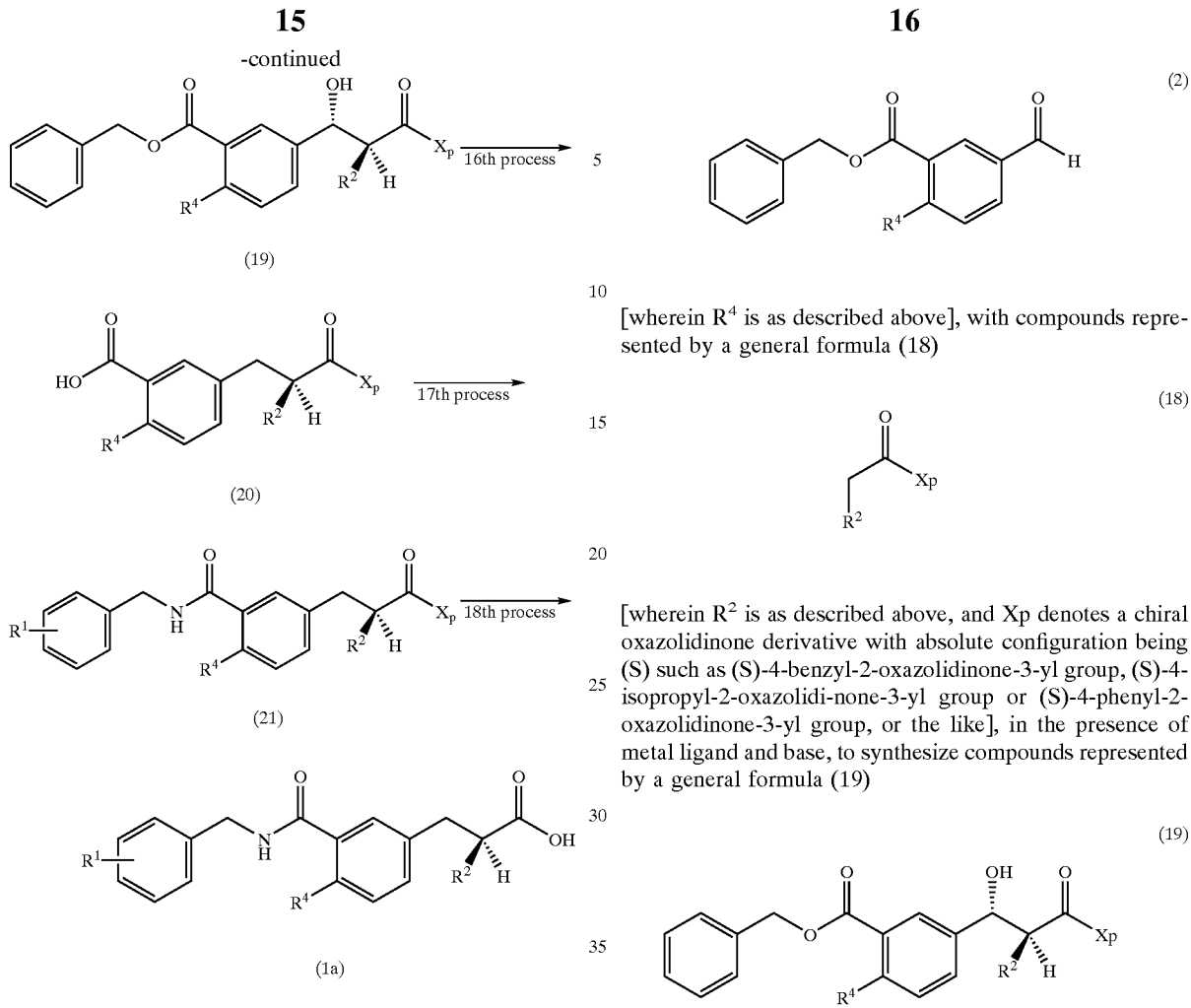

Namely, optically active substituted phenylpropanoic acid derivatives represented by the general formula (1a)

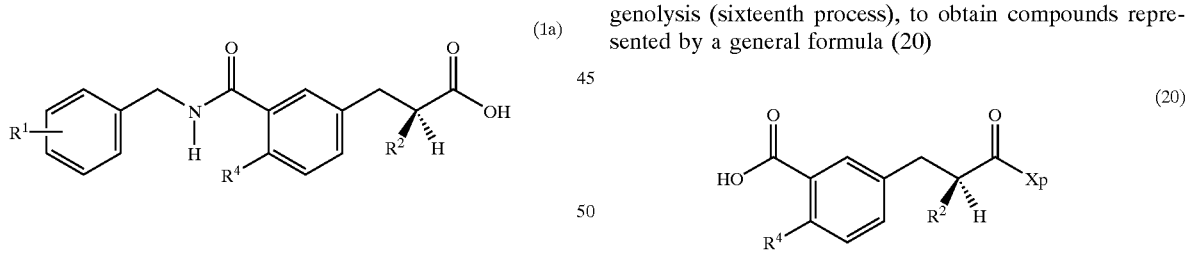

[wherein $R^1$ denotes a lower alkyl group with carbon atoms of 1 to 4, lower alkoxy group with carbon atoms of 1 to 3, trifluoromethyl group, trifluoromethoxy group, phenyl group which is unsubstituted or may have substituents, phenoxy group which is unsubstituted or may have substituents or benzyloxy group which is unsubstituted or may have substituents, $R^2$ denotes a lower alkyl group with carbon atoms of 1 to 4, 2,2,2-trifluoroethyl group, lower alkoxy group with carbon atoms of 1 to 3, phenoxy group, lower alkylthio group with carbon atoms of 1 to 3, phenylthio group or benzylthio group, and $R^4$ denotes a lower alkoxy group with carbon atoms of 1 to 3], can be prepared by reacting (fifteenth process) compounds represented by the general formula (2)

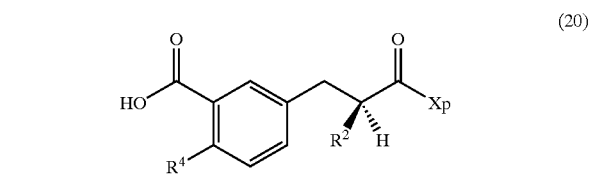

[wherein $R^4$ is as described above], with compounds represented by a general formula (18)

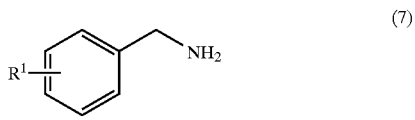

[wherein $R^2$ is as described above, and Xp denotes a chiral oxazolidinone derivative with absolute configuration being (S) such as (S)-4-benzyl-2-oxazolidinone-3-yl group, (S)-4-isopropyl-2-oxazolidi-none-3-yl group or (S)-4-phenyl-2-oxazolidinone-3-yl group, or the like], in the presence of metal ligand and base, to synthesize compounds represented by a general formula (19)

(19)

[wherein $R^2$, $R^4$ and Xp are as described above], by eliminating hydroxyl group of these compounds and hydrogenolysis (sixteenth process), to obtain compounds represented by a general formula (20)

(20)

[wherein $R^2$, $R^4$ and Xp are as described above], by reacting (seventeenth process) these compounds with compounds represented by the general formula (7)

(7)

[wherein $R^1$ is as described above], to obtain compounds represented by a general formula (21)

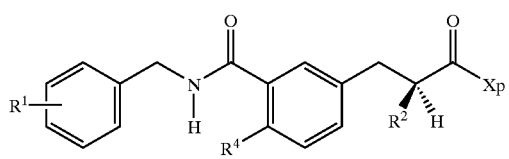

(21)

[wherein $R^1$, $R^2$, $R^4$ and Xp are as described above], and by hydrolyzing (eighteenth process) COXp position of these compounds.

The reaction of the fifteenth process can be performed in a solvent such as tetrahydrofuran, methylene chloride or diethyl ether, using di-n-butylboryltrifurate, diethylboryltrifurate, titanium tetrachloride or the like as a metal ligand and tertiary amine such as triethylamine, diisopropylethylamine or ethyldimethylamine as a base. The reaction can be performed at a reaction temperature of −100° C. to room temperature, preferably −80° C. to 0° C.

The reaction of the sixteenth process can be performed in a solvent such as acetic acid or trifluoroacetic acid in the presence of triethylsilane or trichlorosilane. The reaction can be performed at a reaction temperature of −20° C. to 50° C., preferably 0° C. to room temperature.

The reaction of the seventeenth process can be performed through the process similar to the reaction of the third process.

The reaction of the eighteenth process can be performed under alkaline condition. For alkaline condition, lithium hydroxide, sodium hydroxide, mixture of lithium hydroxide with hydrogen peroxide, or the like is used. The reaction can be performed at a reaction temperature of −20° C. to 100° C., preferably 0° C. to 50° C.

Moreover, optically active compounds being said general formula (1a) can be prepared, for example, through following processes (Scheme 6).

Scheme 6

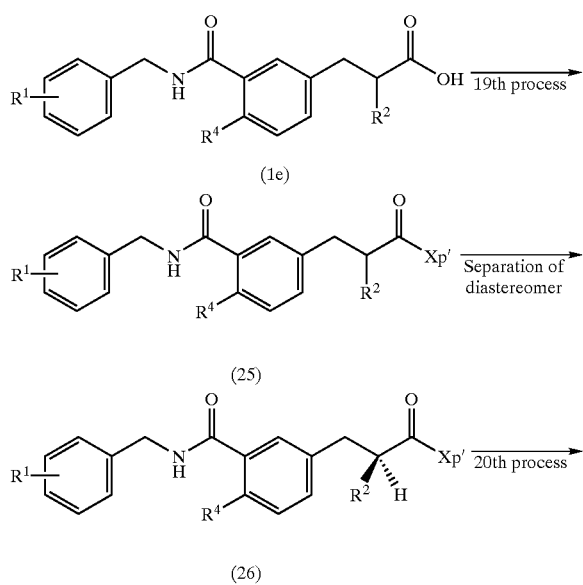

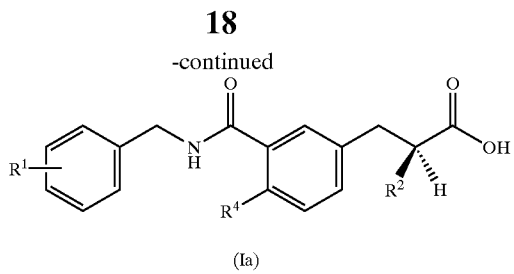

(Ia)

Namely, optically active substituted phenylpropanoic acid derivatives represented by the general formula (1a)

(Ia)

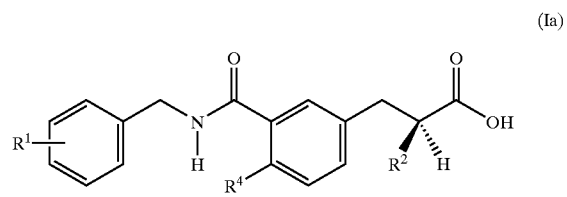

[wherein $R^1$ denotes a lower alkyl group with carbon atoms of 1 to 4, lower alkoxy group with carbon atoms of 1 to 3, trifluoromethyl group, trifluoromethoxy group, phenyl group which is unsubstituted or may have substituents, phenoxy group which is unsubstituted or may have substituents or benzyloxy group which is unsubstituted or may have substituents, $R^2$ denotes a lower alkyl group with carbon atoms of 1 to 4, 2,2,2-trifluoroethyl group, lower alkoxy group with carbon atoms of 1 to 3, phenoxy group, lower alkylthio group with carbon atoms of 1 to 3, phenylthio group or benzylthio group, and $R^4$ denotes a lower alkoxy group with carbon atoms of 1 to 3], can be prepared by reacting compounds represented by the general formula (1e)

(1e)

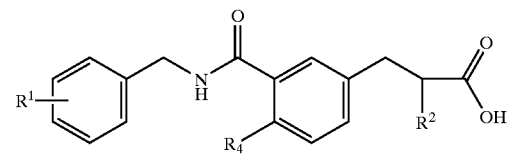

[wherein $R^1$, $R^2$ and $R^4$ are as described above], with pivaloyl chloride in the presence of base, to obtain compounds represented by a general formula (23)

(23)

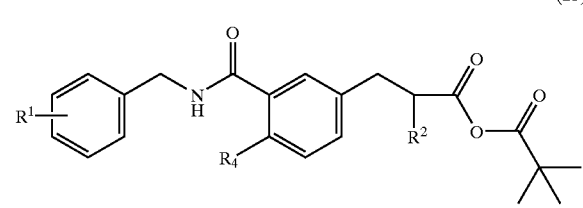

[wherein $R^1$, $R^2$ and $R^4$ are as described above], by reacting (nineteenth process) these compounds with compounds represented by a general formula (24)

(24)

[wherein Xp' denotes an optically active chiral oxazolidinone derivative such as optically active 4-benzyl-2- oxazolidinone-3-yl group, 4-isopropyl-2-oxazolidinone-3-yl group or 4-phenyl-2-oxazolidinone-3-yl group, amide derivative, sultam derivative or the like], in the presence of base, to synthesize compounds represented by a general formula (25)

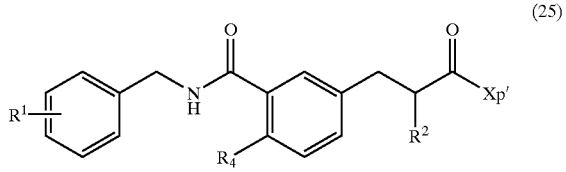

(25)

[wherein $R^1$, $R^2$, $R^4$ and Xp' are as described above], by separating each diastereomer of these compounds by fractional recrystallization or column chromatography, to obtain compounds represented by a general formula (26)

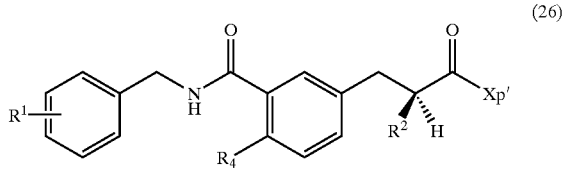

(26)

[wherein $R^1$, $R^2$, $R^4$ and Xp' are as described above], and by hydrolyzing (twentieth process) Xp' portion of these compounds.

In the reaction of the nineteenth process, first, the synthesis of compounds represented by the general formula (23)

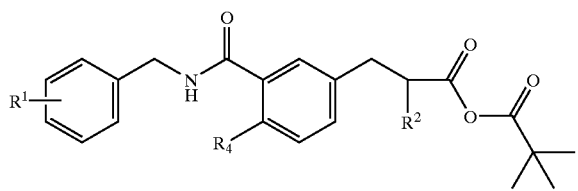

(23)

[wherein $R^1$, $R^2$ and $R^4$ are as described above], can be performes in a solvent such as tetrahydrofuran, methylene chloride or diethyl ether, using tertiary amine such as triethylamine, diisopropylethylamine, ethyldimethylamine or pyridine as a base. The reaction can be performed at a reaction temperature of −100° C. to room temperature, preferably −40° C. to 0° C.

Next, the reaction between general formula (23)

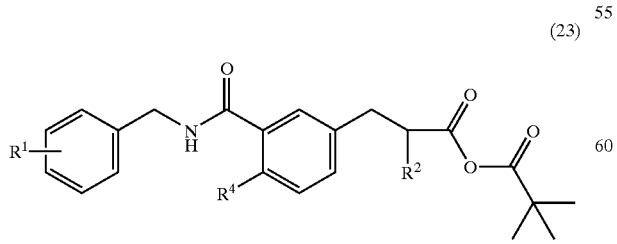

(23)

[wherein $R^1$, $R^2$ and $R^4$ are as described above], and the general formula (24)

$$Xp'—H \quad (24)$$

[wherein Xp' is as described above], can be performed in a solvent such as tetrahydrofuran, methylene chloride or diethyl ether, in the presence of a base of alkali metal hydride such as sodium hydride, organometallic compound such as butyl lithium, metal amide such as lithium diisopropylamide, or metal alkoxide such as sodium methoxide or potassium t-butoxide, or the like. The reaction can be performed at a reaction temperature of −100° C. to room temperature, preferably −40° C. to 0° C.

The reaction of the twentieth process can be performed under alkaline condition. For alkaline condition, lithium hydroxide, sodium hydroxide, mixture of lithium hydroxide with hydrogen peroxide, or the like is used. The reaction can be performed at a reaction temperature of −20° C. to 100° C., preferably 0° C. to 50° C.

Moreover, optically active compounds being said general formula (1a) can also be prepared, for example, through following processes (Scheme 7).

Scheme 7

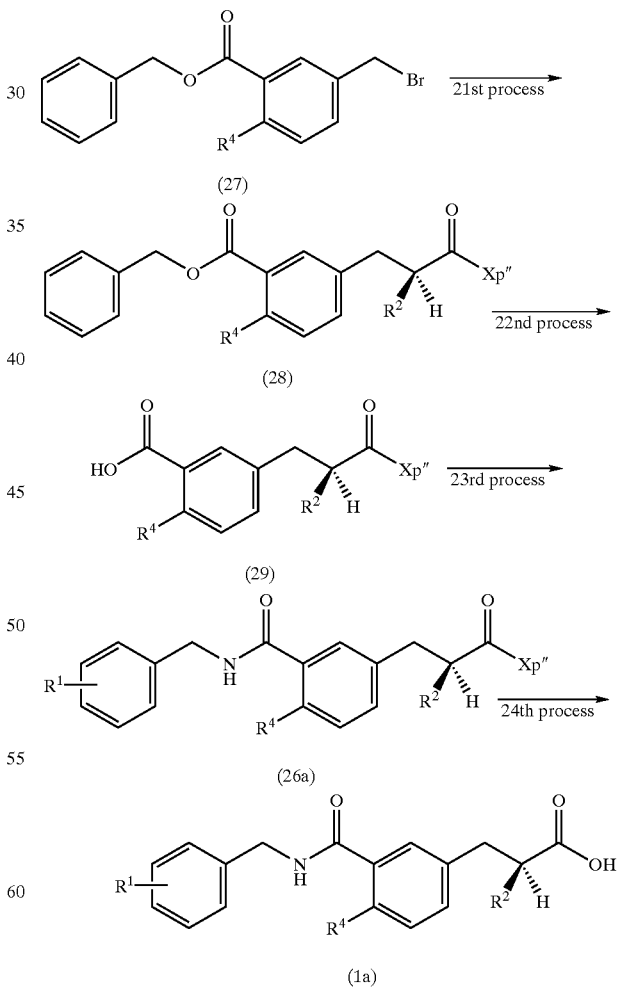

Namely, optically active substituted phenylpropanoic acid derivatives represented by the general formula (1a)

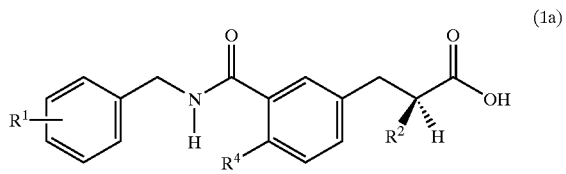

(1a)

[wherein R¹ denotes a lower alkyl group with carbon atoms of 1 to 4, lower alkoxy group with carbon atoms of 1 to 3, trifluoromethyl group, trifluoromethoxy group, phenyl group which is unsubstituted or may have substituents, phenoxy group which is unsubstituted or may have substituents or benzyloxy group which is unsubstituted or may have substituents, R² denotes a lower alkyl group with carbon atoms of 1 to 4, 2,2,2-trifluoroethyl group, lower alkoxy group with carbon atoms of 1 to 3, phenoxy group, lower alkylthio group with carbon atoms of 1 to 3, phenylthio group or benzylthio group, and R⁴ denotes a lower alkoxy group with carbon atoms of 1 to 3], can be prepared by reacting (twenty-first process) compounds represented by a general formula (27)

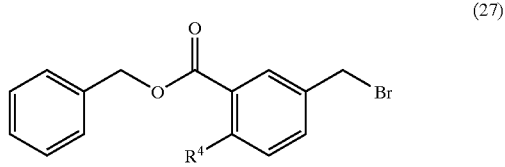

(27)

[wherein R⁴ is as described above], with compounds represented by a general formula (30)

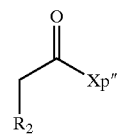

(30)

[wherein R² is as described above, and Xp″ denotes a chiral oxazolidinone with absolute configuration being (R) such as (R)-4-benzyl-2-oxazolidinone-3-yl group, (R)-4-isopropyl-2-oxazolidinone-3-yl-group or (R)-4-phenyl-2-oxazolidinone-3-yl group, chiral imidazolidinone, chiral cyclic lactam, chiral sultam or the like], in the presence of base, to afford compounds represented by a general formula (28)

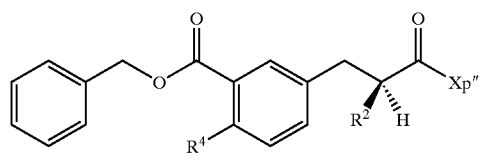

(28)

[wherein R², R⁴ and Xp″ are as described above], which was hydrogenolysed (twenty-second process) in the presence of base to obtain compounds represented by a general formula (29)

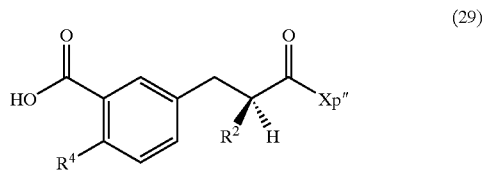

(29)

[wherein R², R⁴ and Xp″ are as described above], by reacting (twenty-third process) these compounds with compounds represented by the general formula (7)

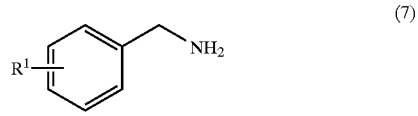

(7)

[wherein R¹ is as described above], to obtain compounds represented by a general formula (26a)

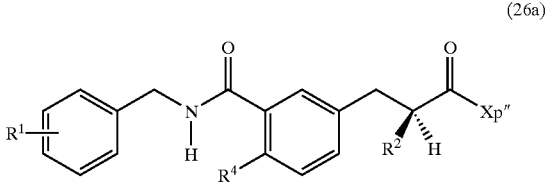

(26a)

[wherein R¹, R², R⁴ and Xp″ are as described above], and by hydrolyzing (twenty-fourth process) COXp″ position of these compounds.

For the reaction of the twenty-first process, for example, alkali metal hydride such as sodium hydride, organometallic compound such as butyl lithium, metal amide such as lithium diisopropylamide or sodium bis(trimethylsilyl) amide can be used as a base in a solvent such as tetrahydrofuran, diethyl ether or hexane. The reaction can be performed at a reaction temperature of −100° C. to room temperature, preferably −80° C. to 0° C.

The reaction of the twenty-second process can be performed at a hydrogen pressure of 98.1 kPa to 491 kPa in a solvent such as ethanol, methanol, tetrahydrofuran, ethyl acetate or N,N-dimethylformamide in the presence of metallic catalyst such as palladium on activated carbon, platinum on activated carbon, platinumoxide or rhodium on alumina. The reaction can be performed at a reaction temperature of 0° C. to 100° C., preferably room temperature to 80° C.

The reaction of the twenty-third process can be performed by leaving carboxyl group as it is or converting it to reactive derivatives. As the "reactive derivative group of carboxyl group", acid chloride, acid bromide, acid anhydride, carbonylimidazole or the like is mentioned.

In the case of the reaction using reactive derivative, the reaction can be performed in a solvent such as dioxane or N,N-dimethylformamide in the presence or absence of, for example, alkali metal hydride such as sodium hydride, alkali metal hydroxide such as sodium hydroxide, alkali metal carbonate such as potassium carbonate, or organic base such as pyridine or triethylamine as a base.

In the case of conducting the reaction by leaving carboxylic acid form as it is, the reaction can be performed in a solvent such as methylene chloride, chloroform, dioxane or N,N-dimethylformamide in the presence of condensing agent in the presence or absence of base, and further in the presence or absence of additive.

As the condensing agent, for example, dicyclohexylcarbodiimide, 1-[3-(dimethylamino)propyl]-3-ethylcarbodiimide hydrochloride, diethyl cyanophosphate, diphenylphosphoric azide, carbonyldiimidazole or the like can be mentioned. As the base, for example, alkali metal hydroxide such as sodium hydroxide, alkali metal carbonate such as potassium carbonate, or organic base such as pyridine or triethylamine can be mentioned. As the additive, N-hydroxybenzotriazole, N-hydroxysuccinimide, 3,4-dihydro-3-hydroxy-4-oxo-1,2,3-benzotriazine or the like can be mentioned. The reaction can be performed at a reaction temperature of −20° C. to 100° C., preferably 0° C. to 50° C.

The reaction of the twenty-fourth process can be performed under alkaline condition. For alkaline condition, lithium hydroxide, sodium hydroxide, mixture of lithium hydroxide with hydrogen peroxide, or the like is used. The reaction can be performed at a reaction temperature of −20° C. to 100° C., preferably 0° C. to 50° C.

As the administrating form of the inventive novel compounds, for example, oral administration with tablet, capsule, granule, powder, inhalant, syrup or the like, or parenteral administration with injection, suppository or the like can be mentioned.

Best embodiment to put the invention into practice

EXAMPLE 1

Ethyl 3-(3-carboxy-4-methoxyphenyl)-2-ethylpropanate

Sodium hydride (214 mg, 5.35 mmol) was suspended in 10 ml of dehydrated tetrahydrofuran under an atmosphere of argon, which was cooled with ice. Triethyl 2-phosphonobutyrate (1.34 g, 5.31 mmol) dissolved in 20 ml of dehydrated tetrahydrofuran was added dropwise. After completion of the dropwise addition, the mixture was stirred for 1 hour. Next, benzyl 5-formyl-2-methoxybenzoate (Referential example 3; 1.44 g, 5.33 mmol) dissolved in 25 ml of dehydrated tetrahydrofuran was added dropwise. After completion of the dropwise addition, the mixture was stirred for 4.5 hours at room temperature. The reaction mixture was poured into ice water, which was extracted with ethyl acetate, washed with water and saturated brine in sequence, then dried over anhydrous sodium sulfate and concentrated. The residue was purified by silica gel chromatography (eluate n-hexane: ethyl acetate=5:1 v/v) to obtain 1.45 g (74%) of ethyl (3-benzyloxy-carbonyl-4-methoxyphenyl)-2-ethylacrylate as a yellow oil.

Mass analysis m/z 368 (M$^+$).

The ethyl (3-benzyloxy-carbonyl-4-methoxyphenyl)-2-ethylacrylate (4.00 g, 10.9 mmol) was dissolved in 200 ml of ethanol, 10% palladium on activated carbon (1.10 g) was added, and medium pressure hydrogenation was performed for 3 hours at an initial pressure of 353 kPa. After completion of the reaction, the catalyst was filtered and the filtrate was concentrated to obtain 3.0 g (98%) of the title compound as a faintly yellow oil.

Mass analysis m/z 280(M$^+$); $^1$H-NMR (400 MHz, CDCl$_3$) δ 0.93(3H,t,J=7.3 Hz), 1.18(3H,t,J=7.3 Hz), 1.52–1.59(1H, m), 1.59–1.70(1H, m), 2.55–2.61(1H,m), 2.76(1H,dd,J=14.2, 6.4 Hz), 2.92(1H,dd,J=14.2, 6.4 Hz), 4.03–4.12(2H, m), 4.06(3H,s), 6.97(1H,d,J=8.8 Hz), 7.38(1H, dd,J=8.8, 2.4 Hz), 8.00(1H,d,J=2.4 Hz).

EXAMPLES 2 THROUGH 6

The compounds listed in Table 1 were obtained similarly to Example 1.

TABLE 1

| Example | R$^2$ | R$^4$ | R$^5$ | Mass analysis (m/z) |
|---|---|---|---|---|
| 2 | CH$_3$ | OCH$_3$ | C$_2$H$_5$ | 266 (M$^+$) |
| 3 | n-C$_3$H$_7$ | OCH$_3$ | C$_2$H$_5$ | 294 (M$^+$) |
| 4 | OCH$_3$ | OCH$_3$ | C$_2$H$_5$ | 282 (M$^+$) |
| 5 | OC$_2$H$_5$ | OCH$_3$ | C$_2$H$_5$ | 296 (M$^+$) |
| 6 | OPh | OCH$_3$ | C$_2$H$_5$ | 344 (M$^+$) |

EXAMPLE 7

Ethyl 2-ethyl-3-[4-methoxy-3-[N-[[4-(trifluoromethyl)phenyl]-methyl]carbamoyl]phenyl] propanoate Ethyl 3-(3-carboxy-4-methoxyphenyl)-2-ethylpropanoate (5.00 g, 17.8 mmol) was dissolved in 80 ml of dehydrated dichloroethane, which was cooled to −10° C. to −15° C. Triethylamine (6.21 ml, 44.5 mmol) was added under stirring. Next, ethyl chlorocarbonate (1.86 ml, 19.5 mmol), dissolved in 10 ml of dehydrated dichloromethane was added dropwise. After stirring for 10 minutes at −10° C., 4-(trifluoromethyl)benzylamine (2.51 ml, 17.8 mmol), dissolved in 10 ml of dehydrated dichloromethane was added dropwise.

After stirring for 30 minutes at −10° C., the mixture was stirred for 7 hours at room temperature and then allowed to stand overnight. The reaction mixture was washed with aqueous solution of citric acid, aqueous solution of sodium hydrogencarbonate and brine in sequence, then dried over anhydrous sodium sulfate and concentrated. The residue was recrystallized from a mixed solvent of n-hexane with ethyl acetate to obtain 7.2 g (93%) of the aimed compound as colorless crystals. Melting point 77.5–79.5° C.;

Mass analysis m/z 437(M$^+$); $^1$H-NMR (400 MHz, CDCl$_3$) δ 0.91(3H,t,J=7.3 Hz), 1.18(3H,t,J=7.3 Hz), 1.51–1.69(2H, m), 2.54–2.61(1H,m), 2.75 (1H,dd,J=13.7, 6.8 Hz), 2.92 (1H,dd,J=13.7, 8.8 Hz), 3.92(3H,s), 4.04–4.12(2H,m), 4.73 (2H,d,J=5.9 Hz), 6.89(1H,d,J=8.8 Hz), 7.25–7.28(1H,m), 7.47(2H,d,J=7.8 Hz), 7.59(2H,d,J=8.3 Hz), 8.06(1H,d,J=2.4 Hz), 8.30(1H,t,J=5.4 Hz).

EXAMPLES 8 THROUGH 19

The compounds listed in Table 2 were obtained similarly to Example 7.

TABLE 2

[Structure with $R^1$, $R^2$, $R^4$, $OR^5$ substituents on benzamide-phenylpropanoate scaffold]

| Example | $R^1$ | $R^2$ | $R^4$ | $R^5$ | Mass analysis (m/z) |
|---|---|---|---|---|---|
| 8 | 4-$CF_3$ | $CH_3$ | $OCH_3$ | $C_2H_5$ | 423 ($M^+$) |
| 9 | 4-$OCH_2Ph$ | $CH_3$ | $OCH_3$ | $C_2H_5$ | 461 ($M^+$) |
| 10 | 4-OPh | $C_2H_5$ | $OCH_3$ | $C_2H_5$ | 461 ($M^+$) |
| 11 | 4-$OCH_2Ph$ | $C_2H_5$ | $OCH_3$ | $C_2H_5$ | 475 ($M^+$) |
| 12 | 4-Ph | $C_2H_5$ | $OCH_3$ | $C_2H_5$ | 445 ($M^+$) |
| 13 | 4-$CF_3$ | $OCH_3$ | $OCH_3$ | $C_2H_5$ | 439 ($M^+$) |
| 14 | 4-$OCH_2Ph$ | $OCH_3$ | $OCH_3$ | $C_2H_5$ | 477 ($M^+$) |
| 15 | 4-OPh | $OCH_3$ | $OCH_3$ | $C_2H_5$ | 463 ($M^+$) |
| 16 | 4-Ph | $OCH_3$ | $OCH_3$ | $C_2H_5$ | 447 ($M^+$) |
| 17 | 4-$OCH_3$ | $OCH_3$ | $OCH_3$ | $C_2H_5$ | 401 ($M^+$) |
| 18 | 4-$CF_3$ | $OC_2H_5$ | $OCH_3$ | $C_2H_5$ | 453 ($M^+$) |
| 19 | 4-$CF_3$ | OPh | $OCH_3$ | $C_2H_5$ | 437 ($M^+$) |

EXAMPLE 20

2-Ethyl-3-[4-methoxy-3-[N-[[4-(trifluoromethyl)phenyl]-methyl]carbamoyl]phenyl]propanoic acid Ethyl 2-ethyl-3-[4-methoxy-3-[N-[[4-(trifluoromethyl)phenyl]methyl]carbamoyl]phenyl]propanoate (1.26 g, 2.88 mmol; Example 7), 15 ml of ethanol and 15 ml of 1 mol/l aqueous solution of sodium hydroxide were mixed and, after stirring for 4 hours at 50° C., the reaction mixture was concentrated under reduced pressure. The residue was dissolved in water, which was made acidic with dilute hydrochloric acid. The precipitates produced were filtered, dried and then recrystallized from ethyl acetate to obtain 1.26 g (95%) of the title compound as colorless prisms. Melting point 144.5–146.5° C.; Mass analysis m/z 409($M^+$); Elemental analysis $C_{21}H_{22}F_3NO_4$(409.40):

Calcd. C, 61.61; H, 5.42; N, 3.42.

Found C, 61.48; H, 5.40; N, 3.41.

$^1$H-NMR (400 MHz, $CDCl_3$) δ0.96(3H,t,J=7.3 Hz), 1.53–1.72(2H,m), 2.59–2.66(1H,m), 2.77(1H,dd,J=13.7, 6.8 Hz), 2.96(1H,dd,J=13.7, 8.3 Hz), 3.92(3H,s), 4.73(2H,d,J=5.9 Hz), 6.90(1H,d,J=8.3 Hz), 7.29(1H,dd,J=8.3, 2.4 Hz), 7.47(2H,d,J=8.3 Hz), 7.59(2H,d,J=7.8 Hz), 8.08 (1H,d,J=2.4 Hz), 8.32(1H,t,J=5.9 Hz).

EXAMPLES 21–31

The compounds listed in Table 3 were obtained similarly to Example 20.

TABLE 3

[Structure with $R^1$, $R^2$, $R^4$ substituents and free carboxylic acid]

| Example | $R^1$ | $R^2$ | $R^4$ | Melting point (° C.) | Charac. formula | Elemental analysis (%) |
|---|---|---|---|---|---|---|
| 21 | 4-$OCH_2Ph$ | $C_2H_5$ | $OCH_3$ | 127.0–122.5 | $C_{27}H_{29}NO_5$ | Calcd.; C 72.46, H 65.3, N 3.13 |
| | | | | | | Found; C 72.30, H 6.55, N 3.14 |
| 22 | 4-Ph | $C_2H_5$ | $OCH_3$ | 158.5–159.5 | $C_{26}H_{27}NO_4$ | Calcd.; C 74.80, H 6.52, N 3.35 |
| | | | | | | Found; C 74.87, H 6.63, N 3.34 |
| 23 | 4-OPh | $C_2H_5$ | $OCH_3$ | 127.0–128.0 | $C_{28}H_{27}NO_5$ | Calcd.; C 72.04, H 6.28, N 3.23 |
| | | | | | | Found; C 71.86, H 6.31, N 3.21 |
| 24 | 4-$CF_3$ | $OCH_3$ | $OCH_3$ | 161.0–163.0 | $C_{20}H_{20}F_3NO_5$ | Calcd.; C 58.39, H 4.90, N 3.40 |
| | | | | | | Found; C 58.35, H 4.82, N 3.49 |
| 25 | 4-$OCH_2Ph$ | $OCH_3$ | $OCH_3$ | 136.0–138.0 | $C_{26}H_{27}NO_6$ | Calcd.; C 69.47, H 6.05, N 3.12 |
| | | | | | | Found; C 69.38, H 6.09, N 3.16 |
| 26 | 4-Ph | $OCH_3$ | $OCH_3$ | 176.0–178.0 | $C_{25}H_{25}N_5$ | Calcd.; C 71.58, H 6.01, N 3.34 |
| | | | | | | Found; C 71.56, H 6.15, N 3.36 |
| 27 | 4-OPh | $OCH_3$ | $OCH_3$ | 137.5–139.0 | $C_{25}H_{25}NO_6$ | Calcd.; C 68.95, H 5.79, N 3.22 |
| | | | | | | Found; C 68.74, H 5.80, N 3.23 |
| 28 | 4-$OCH_3$ | $OCH_3$ | $OCH_3$ | 128.5–129.5 | $C_{20}H_{23}NO_6$ | Calcd.; C 64.33, H 6.21, N 3.75 |
| | | | | | | Found; C 64.22, H 6.22, N 3.79 |
| 29 | 4-$CF_3$ | $OC_2H_5$ | $OCH_3$ | 146.0–148.0 | $C_{21}H_{22}F_3NO_5$ | Calcd.; C 59.29, H 5.21, N 3.29 |
| | | | | | | Found; C 59.04, H 5.10, N 3.33 |
| 30 | 4-$CF_3$ | $CH_3$ | $OCH_3$ | 155.0–156.0 | $C_{20}H_{20}F_3NO_4$ | Calcd.; C 60.76, H 5.10, N 3.54 |
| | | | | | | Found; C 60.77, H 5.12, N 3.57 |
| 31 | 4-$CF_3$ | OPh | $OCH_3$ | 141.5–143.0 | $C_{25}H_{22}F_3NO_5$ | Calcd.; C 63.42, H 4.68, N 2.96 |
| | | | | | | Found; C 63.25, H 4.70, N 2.93 |

Referential Example 1

5-Formyl-2-methoxy-N-[[4-(trifluoromethyl)phenyl]methyl]-benzamide

Publicly known [e.g. E. J. Wayne et al, J. Chem. Soc., 1022(1922)] 5-formyl-2-methoxybenzoic acid (4.05 g, 22.5 mmol) was dissolved in 80 ml of dichloromethane, which was cooled with ice. Triethylamine (7.94 ml, 56.2 mmol) was added under stirring. Next, ethyl chlorocarbonate (2.44 ml, 24.8 mmol) was added and, after stirring for 10 minutes, 4-(trifluoromethyl)benzylamine (3.31 ml, 22.5 mmol) was added dropwise, which was allowed to stand overnight. After washed with water, the reaction mixture was dried over anhydrous sodium sulfate and concentrated. Water was added to the residue, which was made acidic with dilute hydrochloric acid. Then, the precipitates were filtered and dried to quantitatively obtain the title compound as milky white crystals.

Mass analysis m/z 337($M^+$).

EXAMPLE 32

Ethyl 2-methoxy-3-[4-methoxy-3-[N-[[4-(trifluoromethyl)phenyl]methyl]carbamoyl]phenyl]acrylate Ethyl 2-(diethoxyphosphoryl)-2-methoxyacetate (265 mg, 1.10 mmol) was dissolved in 3 ml of dehydrated tetrahydrofuran and potassium t-butoxide (123 mg, 1.10 mmol) was added under stirring and cooling with ice under an atmosphere of argon, which was stirred for 30 minutes. Next, N-[[4-(trifluoromethyl)phenyl]methyl]-5-formyl-2-methoxybenzamide (338 mg, 1.00 mmol) dissolved in 2 ml of dehydrated tetrahydrofuran was added. After stirring for 1 hour at room temperature, the reaction mixture was poured into ice water, which was extracted with ethyl acetate, washed with water and brine in sequence, then dried over anhydrous sodium sulfate and concentrated. The residue was purified by silica gel chromatography (eluate n-hexane:ethyl acetate=3:1 v/v) to obtain 330 mg (78%) of the title compound (mixture of geometrical isomers relevant to double bond) as colorless crystals.

Mass analysis m/z 423($M^+$).

EXAMPLE 33

Ethyl 2-methoxy-3-[4-methoxy-3-[N-[[4-(trifluoromethyl)phenyl]methyl]carbamoyl]phenyl]propanoate Ethyl 2-methoxy-3-[4-methoxy-3-[N-[[4-(trifluoromethyl)phenyl]methyl]carbamoyl]phenyl]acrylate (150 mg, 0.354 mmol), 2.5 ml of ethanol and 2.5 ml of tetrahydrofuran were mixed, 10% palladium on activated carbon (30 mg) was added thereto, and normal pressure hydrogenation was conducted for 7.5 hours at room temperature. After completion of the reaction, the catalyst was filtered and the filtrate was concentrated to obtain 148 mg (98%) of the title compound as colorless crystals.

Mass analysis m/z 425($M^+$).

Referential Example 2

2-Methoxy-5-nitro-N-[[4-(trifluoromethyl)phenyl]methyl]-benzamide

Publicly known [e.g. De.Paulis et al, J. Med. Chem., 1022(1922)]2-methoxy-5-nitrobenzoic acid (9.00 g, 45.7 mmol) was dissolved in 450 ml of dichloromethane and, after triethylamine (8.11 ml, 58.4 mmol) and ethyl chlorocarbonate (4.70 ml, 49.3 mmol) were added, the mixture was stirred for 45 minutes at room temperature. Next, 4-trifluoromethylbenzylamine (9.59 g, 54.8 mmol) was added dropwise, which was stirred for 30 minutes at room temperature. The reaction mixture was poured into water. The organic layer was separated, dried over anhydrous magnesium sulfate and concentrated. The residue was recrystallized from ethyl acetate to obtain 12.5 g of the aimed compound as yellow powder. Further, the filtrate was concentrated and recrystallized from ethyl acetate to obtain 2.13 g of the second crystals. Total 14.6 g (91%).

Mass analysis m/z 354($M^+$); $^1$H-NMR (400 MHz, $CDCl_3$) δ4.09(3H,s), 4.75(2H,d,J=5.9 Hz), 7.11(1H,d,J=8.8 Hz), 7.47(2H,d,J=7.8 Hz), 7.61 (2H,d,J=7.8 Hz), 8.05(1H,brs), 8.36(1H,dd,J=8.8, 3.0 Hz), 9.12(1H,d, J=3.0 Hz).

EXAMPLE 34

5-Amino-2-methoxy-N-[[4-(trifluoromethyl)phenyl]methyl]-benzamide

2-Methoxy-5-nitro-N-[[4-(trifluoromethyl)phenyl]methyl]-benzamide (14.6 g, 41.2 mmol) and 146 ml of ethyl acetate were mixed and, after 10% palladium on activated carbon (2.6 g) was added, the mixture was stirred for 5 hours at room temperature. Catalyst was filtered, washed with ethyl acetate, and the reaction mixture was concentrated. The residue was recrystallized from a mixed solvent of n-hexane with ethyl acetate to obtain 12.4 g (93%) of the title compound as colorless crystals.

Mass analysis m/z 324($M^+$); $^1$H-NMR (400 MHz, $CDCl_3$) δ3.87(3H,s), 4.72(2H,d,J=5.9 Hz), 6.80(1H,dd,J=8.8, 3.0 Hz), 6.83(1H,d,J=8.8 Hz), 7.46(2H,d,J=7.8 Hz), 7.59(3H, m), 8.43(1H,brs).

EXAMPLE 35

Ethyl 2-bromo-3-[4-methoxy-3-[N-[[4-(trifluoromethyl)phenyl]methyl]carbamoyl]phenyl]propanoate 5-Amino-2-methoxy-N-[[4-(trifluoromethyl)phenyl]-methyl]benzamide (7.00 g, 21.6 mmol), 85 ml of acetone and 34 ml of methanol were mixed, which was cooled with ice. Under stirring, 17.5 ml of 47% hydrobromic acid, sodium nitrite (1.65 g, 23.9 mmol) and 6.2 ml of water were added and the mixture was stirred for 10 minutes. Next, ethyl acrylate (13.4 ml, 128 mmol) and copper oxide (I) (416 mg, 2.91 mmol) were added at room temperature. After stirring for 30 minutes, the reaction mixture was poured into saturated aqueous solution of sodium hydrogencarbonate, which was extracted with ethyl acetate. The extract was washed with brine, then dried over anhydrous magnesium sulfate and concentrated. The residue was recrystallized from a mixed solvent of n-hexane with ethyl acetate to obtain 683 mg (71%) of the title compound as colorless crystals.

Mass analysis m/z 469($M^+$); $^1$H-NMR (400 MHz, $CDCl_3$) δ1.21–1.26(6H, m), 2.61–2.67(2H,m), 2.96(1H,dd,J=14.2, 6.8 Hz), 3.18(1H,dd,J=14.2, 9.3 Hz), 3.53(1H,dd,J=9.3, 6.8 Hz), 3.93(3H,s), 4.10–4.19(2H,m), 4.73 (2H,d,J=5.9 Hz), 6.91(1H,d,J=8.3 Hz), 7.32(1H,dd,J=8.3, 2.4 Hz), 7.47(2H, d,J=7.8 Hz), 7.59(2H,d,J=7.8 Hz), 8.11(1H,d,J=2.4 Hz), 8.30 (1H,brs).

EXAMPLE 36

Ethyl 2-ethylthio-3-[4-methoxy-3-[N-[[4-(trifluoromethyl)phenyl]methyl]carbamoyl]phenyl]propanoate Ethyl 2-bromo-3-[4-methoxy-3-[N-[[4-(trifluoromethyl)phenyl]methyl]carbamoyl]phenyl]propanoate (1.00 g, 2.05 mmol; Example 37) and 56 ml of ethanol were mixed and, after sodium thioethoxide (268 mg, 2.55 mmol) was added under stirring, the mixture was refluxed for 1.5 hours. The reaction mixture was concentrated, water was added, and the solution was extracted with ethyl acetate. The extract was washed with brine, then dried over anhydrous magnesium sulfate and concentrated. The residue was purified by silica gel chromatography (eluate n-hexane:ethyl acetate=2:1 v/v) to obtain 3.4 g (43%) of the title compound as colorless crystals.

Mass analysis m/z 324(M$^+$); $^1$H-NMR (400 MHz, CDCl$_3$) δ 3.87(3H,s), 4.72(2H,d,J=5.9 Hz), 6.80(1H,dd,J=8.8, 3.0 Hz), 6.83(1H,d,J=8.8 Hz), 7.46(2H,d,J=7.8 Hz), 7.59(3H, m), 8.43(1H,brs).

EXAMPLES 37 AND 38

The compounds listed in Table 4 were obtained similarly to Example 36.

TABLE 4

| Example | R$^1$ | R$^2$ | R$^4$ | R$^5$ | Mass analysis (m/z) |
|---|---|---|---|---|---|
| 37 | 4-CF$_3$ | SPh | OCH$_3$ | C$_2$H$_5$ | 517 (M$^+$) |
| 38 | 4-CF$_3$ | SCH$_2$Ph | OCH$_3$ | C$_2$H$_5$ | 531 (M$^+$) |

EXAMPLES 39 THROUGH 41

Compounds in Table 5 were obtained similarly to Example 20.

Table 5

| Example | R$^1$ | R$^2$ | R$^4$ | Melting point (° C.) | Charac. formula | Elemental analysis (%) | |
|---|---|---|---|---|---|---|---|
| 39 | 4-CF$_3$ | SC$_2$H$_5$ | OCH$_3$ | 155.0–157.0 | C$_{21}$H$_{22}$F$_3$NO$_4$S | Calcd.; | C 57.13, H 5.02, N 3.17 |
| | | | | | | Found; | C 56.79, H 4.89, N 3.15 |
| 40 | 4-CF$_3$ | SPh | OCH$_3$ | 130.0–131.5 | C$_{25}$H$_{22}$F$_3$NO$_4$S | Calcd.; | C 61.34, H 4.53, N 2.86 |
| | | | | | | Found; | C 61.08, H 4.45, N 2.82 |
| 41 | 4-CF$_3$ | SCH$_2$Ph | OCH$_3$ | Foam | C$_{21}$H$_{22}$F$_3$NO$_4$S | Calcd.; | C 62.02, H 4.80, N 2.78 |
| | | | | | | Found; | C 62.39, H 5.03, N 2.72 |

Referential Example 3

Benzyl 5-acetoxymethyl-2-methoxybenzoate

5-Formyl-2-methoxybenzoic acid (1.76 g, 9.77 mmol), benzylbromide (1.26 ml, 10.3 mmol), potassium hydrogencarbonate (2.94 g, 29.3 mmol) and 40 ml of N,N-dimethylformamide were mixed and the mixture was stirred for 4 hours at room temperature, then the insolubles were filtered. Ethyl acetate was added to the filtrate, which was washed with water and with brine, then dried over anhydrous sodium sulfate and concentrated to quantitatively obtain benzyl 5-formyl-2-methoxybenzoate.

Mass analysis m/z 270(M$^+$); Melting point 58.5–59.5° C.

Benzyl 5-formyl-2-methoxybenzoate (1.10 g, 4.07 mmol) and 30 ml of methanol were mixed and sodium borohydride (155 mg, 4.10 mmol) was added little by little under stirring and cooling with ice. After stirring for 2 hours under cooling with ice, the reaction mixture was poured into ice water and made acidic with 1 mol/l hydrochloric acid, which was extracted with ethyl acetate. The extract was washed with water and with brine, then dried over anhydrous sodium sulfate and concentrated to obtain 1.11 g (99%) of benzyl 5-hydroxymethyl-2-methoxybenzoate (without purifying further, this compound was used for the next reaction).

Next, benzyl 5-hydroxymethyl-2-methoxybenzoate and 100 ml of methylene chloride were mixed and, after pyridine (660 ml, 8.16 mmol), acetic anhydride (460 ml, 4.88 mmol) and N,N-dimethylaminopyridine (25 mg, 0.205 mmol) were added under stirring and cooling with ice, the mixture was stirred overnight. The reaction mixture was washed with 1 mol/l hydrochloric acid, aqueous solution of sodium hydrogencarbonate and brine, then dried over anhydrous sodium sulfate and concentrated to obtain 1.27 g (99%) of the title compound as a colorless oil.

Mass analysis m/z 314(M$^+$); $^1$H-NMR (400 MHz, CDCl$_3$) δ2.08(3H,s), 3.91(3H,s), 5.03(2H,s), 5.35(2H,s), 6.97(1H,d, J=8.3 Hz), 7.31–7.50 (6H,m), 7.83(1H,d,J=2.4 Hz).

EXAMPLE 42

Methyl 3-(3-benzyloxycarbonyl-4-methoxyphenyl)-2,2-dimethylpropanoate

Benzyl 5-acetoxymethyl-2-methoxybenzoate (630 mg, 2.00 mmol), methyl trimethylsilyldimethylketeneacetal (730 mg, 4.02 mmol) and 25 ml of dehydrated methylene chloride were mixed and magnesium perchlorate (45 mg, 0.202 mmol) was added under an atmosphere of argon, which was stirred for 6 hours at room temperature. The reaction mixture was washed with water and with brine, then dried over anhydrous sodium sulfate and concentrated. The residue was purified by silica gel chromatography (eluate n-hexane:ethyl acetate=8:1 v/v) to obtain 131 mg (18%) of the title compound as colorless crystals.

Mass analysis m/z 356(M$^+$); $^1$H-NMR (400 MHz, CDCl$_3$) δ1.16(6H,s), 2.79(2H,s), 3.56(3H,s), 3.88(3H,s), 5.33(2H,s), 6.88(1H,d,J=8.8 Hz), 7.20(1H,dd,J=8.3, 2.4 Hz), 7.30–7.47 (5H,m), 7.56(1H,d,J=2.4 Hz).

EXAMPLE 43

Methyl 3-(3-carboxy-4-methoxyphenyl)-2,2-dimethylpropionate

Methyl 3-(3-benzyloxycarbonyl-4-methoxyphenyl)-2,2-dimethylpropanoate (310 mg, 0.870 mmol) was dissolved in 7 ml of mixed solvent of ethanol with tetrahydrofuran at a ratio of 1:1, 10% palladium on activated carbon (20 mg) was added thereto, and normal pressure hydrogenation was conducted for 5 hours. After completion of the reaction, catalyst was filtered and the filtrate was concentrated to obtain 290 mg (90%) of the title compound as a colorless oil.

Mass analysis m/z 266(M$^+$); $^1$H-NMR (400 MHz, CDCl$_3$) δ1.18(6H,s), 2.85(2H,s), 3.68(3H,s), 4.06(3H,s), 6.96(1H,d, J=8.3 Hz), 7.31(1H,dd,J=8.3,2.0 Hz), 7.94(1H,d,J=2.0 Hz), 10.46–11.00(1H,brs).

EXAMPLE 44

Methyl 3-[4-methoxy-3-[N-[[4-(trifluoromethyl)phenyl]methyl]carbamoyl]phenyl]-2,2-dimethylpropanoate Using methyl 3-(3-carboxy-4-methoxyphenyl)-2,2-dimethylpropanoate (204 mg, 0.766 mmol), triethylamine (135 ml, 0.969 mmol), ethyl chlorocarbonate (82.0 ml, 0.843 mmol), 4-(trifluoromethyl)benzylamine (120 ml, 0.842 mmol) and 8 ml of dehydrated dichloromethane and conducting the procedure similar to Example 7, 309 mg (95%) of the title compound were obtained as a colorless oil.

Mass analysis m/z 423(M$^+$); $^1$H-NMR (400 MHz, CDCl$_3$) δ1.18(6H,s), 2.85(2H,s), 3.69(3H,s), 3.92(3H,s), 4.73(2H,d, J=5.9 Hz), 6.89(1H,d,J=8.3 Hz), 7.20(1H,dd,J=8.3, 2.4 Hz), 7.47(2H,d,J=7.8 Hz), 7.59(2H, d,J=7.8 Hz), 7.99(1H,d,J=2.4 Hz), 8.29(1H,brs).

EXAMPLE 45

3-[4-Methoxy-3-[N-[[4-(trifluoromethyl)phenyl]methyl]carbamoyl]phenyl]-2,2-dimethylpropanoic acid Using methyl 3-[4-methoxy-3-[N-[[4-(trifluoromethyl)phenyl]methyl]carbamoyl]phenyl]-2,2-dimethylpropanoate (300 mg, 0.708 mmol; Example 47), ethanol (5 ml) and 10% aqueous solution of sodium hydroxide (2 ml) and conducting the procedure similar to Example 22, 206 mg (90%) of the title compound were obtained as colorless crystals.

Melting point 151.0–152.0° C.; Mass analysis m/z 409 (M$^+$);

Elemental analysis C$_{21}$H$_{22}$F$_3$NO$_4$ (409.40):

Calcd. C, 61.61; H, 5.42; N, 3.42.

Found C, 61.68; H, 5.45; N, 3.48.;

$^1$H-NMR (400 MHz, DMSO-d$_6$) δ1.06(6H,s), 2.96(2H,s), 3.88(3H,s), 4.56 (2H,d,J=6.4 Hz), 7.06(1H,d,J=8.8 Hz), 7.25(1H,dd,J=8.8, 2.4 Hz), 7.51–7.58(2H,m), 7.70(1H,d,J=7.8 Hz), 8.80(1H,t,J=5.9 Hz), 12.24(1H, s).

Referential Example 4

(S)-4-benzyl-3-butyryl-2-oxazolidinone (S)-4-benzyl-2-oxazolidinone (2.26 g, 15.0 mmol) and 30 ml of dehydrated tetrahydrofuran were mixed, which was cooled to −78° C. under an atmosphere of argon. Under stirring, 1.6 mol/l solution of n-butyl lithium in hexane (10.3 ml, 16.5 mmol) was added dropwise for over 10 minutes and the mixture was stirred for 30 minutes as it was. Next, butyryl chloride (1.56 ml, 15.0 mmol) dissolved into 30 ml of dehydrated tetrahydrofuran was added dropwise for over 10 minutes and the mixture was stirred for 30 minutes, followed by stirring for 3 hours at room temperature. Saturated aqueous solution of ammonium chloride was added to the reaction mixture and concentrated. Water was added to the residue, which was extracted with ethyl acetate. The extract was washed with water and with brine, then dried over anhydrous sodium sulfate and concentrated. The residue was purified by silica gel chromatography (eluate n-hexane:ethyl acetate=1:1 v/v) to obtain 3.64 g (98%) of the title compound as a colorless oil.

Mass analysis m/z 247(M$^+$).

EXAMPLE 46

(+)-2-ethyl-3-[4-methoxy-3-[N-[[4-(trifluoromethyl)phenyl]methyl]carbamoyl]phenyl]propanoic acid (S)-4-benzyl-3-butyryl-2-oxazolidinone (1.65 g, 6.68 mmol) was dissolved in 22 ml of dehydrated methylene chloride, which was cooled to −74° C. under an atmosphere of argon. After triethylamine (1.11 ml, 8.02 mmol) was added, 1.0 mol/l solution of dibutylboryltrifurate in methylene chloride (7.35 ml, 7.35 mmol) was added dropwise over 15 minutes, which was stirred for 30 minutes. Next, after stirring for 50 minutes under cooling with ice, the mixture was cooled to −75° C. Following this, benzyl 5-formyl-2-methoxybenzoate (1.81 g, 6.68 mmol) dissolved into 56.5 ml of dehydrated methylene chloride was added dropwise over 20 minutes. After stirring for 1.5 hours at −75° C., the mixture was stirred for 2 hours under cooling with ice. A mixed solution comprising 30 ml of methanol, 16.7 ml of phosphate buffer and 7.3 ml of 30% aqueous hydrogen peroxide was added and the mixture was stirred further for 30 minutes at 0° C. The reaction mixture was poured into water, which was extracted with methylene chloride. The extract was washed with brine, then dried over anhydrous magnesium sulfate and concentrated. The residue was purified by silica gel chromatography (eluate n-hexane:ethyl acetate=3:2 v/v) to obtain 1.36 g (39%) of (4S)-3-[3-(3-benzyloxycarbonyl-4-methoxyphenyl)-2-ethyl-3-hydroxypropionyl]-4-benzyl-2-oxazolidinone.

Mass analysis m/z 518(M+1)$^+$.

Next, (4S)-3-[3-(3-benzyloxycarbonyl-4-methoxyphenyl)-2-ethyl-3-hydroxypropionyl]-4-benzyl-2-oxazolidinone (1.35 g, 2.61 mmol) and 22 ml of trifluoroacetic acid were mixed under cooling with ice and triethylsilane (3.95 ml, 26.1 mmol) was added over 5 minutes. The mixture was stirred for 1 hour under cooling with ice, followed by stirring for 4 days at room temperature. The reaction mixture was concentrated and the residue was poured into 0.5 mol/l aqueous solution of sodium hydroxide, which was washed with ethyl acetate. The aqueous layer was made acidic and extracted with methylene chloride. The extract was washed with brine, then dried over anhydrous magnesium sulfate and concentrated to obtain 1.34 g of crude (4S)-3-[3-(3-carboxy-4-methoxyphenyl)-2-ethylpropionyl]-4-benzyl-2-oxazolidinone as a yellow oil. This compound was used for next reaction without purifying further.

Using crude (4S)-3-[3-(3-carboxy-4-methoxyphenyl)-2-ethylpropionyl]-4-benzyl-2-oxazolidinone (1.34 g), triethylamine (435 ml, 3.13 mmol), ethyl chlorocarbonate (275 ml, 2.87 mmol), 4-(trifluoromethyl)benzylamine (686 mg, 3.92 mmol) and 33 ml of methylene chloride and conducting the procedure similar to Example 7, 860 mg (58%) of (4S)-3-[2-ethyl-3-[4-methoxy-3-[N-[[4-(trifluoromethyl)phenyl]methyl]-carbamoyl]phenyl]propionyl]-4-benzyl-2-oxazolidinone as colorless powder.

Mass analysis m/z 568(M⁺); ¹H-NMR (400 MHz, CDCl₃) δ 0.98(3H,t,J=7.3 Hz), 1.58–1.65(1H,m), 1.80–1.87(1H,m), 2.71(1H,dd,J=13.2, 9.8 Hz), 2.78(1H,dd,J=13.2, 6.4 Hz), 3.00(1H,dd,J=13.7, 8.3 Hz), 3.30(1H,dd,J=13.7, 2.9 Hz), 3.92(3H,s), 3.98–4.07(3H,m), 4.61–4.67(1H, m), 4.71(2H, d,J=5.9 Hz), 6.90(1H,d,J=8.3 Hz), 7.20–7.37(6H,m), 7.44 (2H,d,J=7.8 Hz), 7.57(2H,d,J=7.8 Hz), 8.00(1H,d,J=2.5 Hz), 8.24(1H,t,J=5.9 Hz).

(4S)-3-[2-ethyl-3-[4-methoxy-3-[N-[[4-(trifluoromethyl)phenyl]methyl]carbamoyl]phenyl]propionyl]-4-benzyl-2-oxazolidinone (860 mg, 1.51 mmol) was mixed with 8 ml of mixed solution of tetrahydrofuran with water (4:1 v/v), which was cooled with ice under an atmosphere of argon. Under stirring, 611 ml of 30% aqueous hydrogen peroxide was added over 2 minutes, further 101 mg of lithium hydroxide monohydrate dissolved in 2.7 ml of water was added thereto over 2 minutes. After the mixture was stirred for 1 hour under cooling with ice, sodium sulfite 7-hydrate dissolved in 4 ml of water was added, and the mixture was stirred for 5 minutes at 0° C. The reaction mixture was poured into 5% aqueous solution of hydrochloric acid, which was extracted with ethyl acetate. The extract was washed with brine, then dried over anhydrous magnesium sulfate and concentrated. The residue was crystallized by adding ethyl acetate and n-hexane to obtain 125 mg (20%) of the title compound as colorless prisms.

Melting point 128.0–130.0° C.; Mass analysis m/z 409 (M⁺);

Elemental analysis C₂₁H₂₂F₃NO₄ (409.40):

Calcd. C, 61.61; H, 5.42; N, 3.42.

Found C, 61.48; H, 5.40; N, 3.41.;

¹H-NMR (400 MHz, CDCl₃) δ0.96(3H,t,J=7.3 Hz), 1.55–1.71(2H,m), 2.61–2.67(1H,m), 2.77(1H,dd,J=13.7, 6.4 Hz), 2.96(1H,dd,J=13.7, 7.8 Hz), 3.92(3H,s), 4.73(2H,d,J= 5.9 Hz), 6.90(1H,d,J=8.3 Hz), 7.29 (1H,dd,J=8.3, 2.4 Hz), 7.46 (2H,d,J=8.3 Hz), 7.59(2H,d,J=8.3 Hz), 8.08(1H,d,J=2.4 Hz), 8.32(1H,t,J=5.9 Hz).

Specific rotation [α]_D²⁵+23°(C 0.4, MeOH); Optical purity 88% e.e. (from HPLC analysis using Chiral PAC AD).

EXAMPLES 47 AND 48

The compounds listed in Table 6 were obtained similarly to Example 1.

TABLE 6

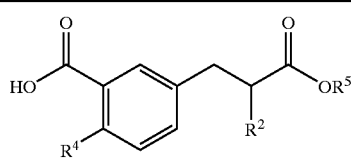

| Example | R² | R⁴ | R⁵ | Mass analysis (m/z) |
|---|---|---|---|---|
| 47 | i-C₃H₇ | OCH₃ | C₂H₅ | 294 (M⁺) |
| 48 | n-C₄H₉ | OCH₃ | C₂H₅ | 308 (M⁺) |

EXAMPLES 49 THROUGH 94

The compounds listed in Table 7 were obtained similarly to Example 7.

TABLE 7

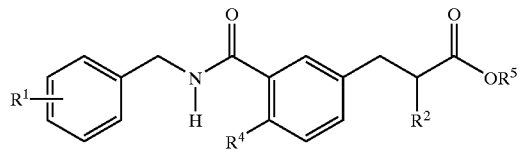

| Example | R¹ | R² | R⁴ | R⁵ | Mass analysis (m/z) |
|---|---|---|---|---|---|
| 49 | 4-CF₃ | n-C₃H₇ | OCH₃ | C₂H₅ | 451 (M⁺) |
| 50 | 4-OPh | n-C₃H₇ | OCH₃ | C₂H₅ | 475 (M⁺) |
| 51 | 4-OCH₂Ph | n-C₃H₇ | OCH₃ | C₂H₅ | 489 (M⁺) |
| 52 | 4-Ph | n-C₃H₇ | OCH₃ | C₂H₅ | 459 (M⁺) |
| 53 | 4-CF₃ | i-C₃H₇ | OCH₃ | C₂H₅ | 451 (M⁺) |
| 54 | 4-OPh | i-C₃H₇ | OCH₃ | C₂H₅ | 475 (M⁺) |
| 55 | 4-OCH₂Ph | i-C₃H₇ | OCH₃ | C₂H₅ | 489 (M⁺) |
| 56 | 4-Ph | i-C₃H₇ | OCH₃ | C₂H₅ | 459 (M⁺) |
| 57 | 4-CF₃ | n-C₄H₉ | OCH₃ | C₂H₅ | 465 (M⁺) |
| 58 | 4-OPh | n-C₄H₉ | OCH₃ | C₂H₅ | 489 (M⁺) |
| 59 | 4-OCH₂Ph | n-C₄H₉ | OCH₃ | C₂H₅ | 503 (M⁺) |
| 60 | 4-Ph | n-C₄H₉ | OCH₃ | C₂H₅ | 473 (M⁺) |
| 61 | 2-OPh | C₂H₅ | OCH₃ | C₂H₅ | 461 (M⁺) |
| 62 | 3-OPh | C₂H₅ | OCH₃ | C₂H₅ | 461 (M⁺) |
| 63 | 2-OPh | n-C₃H₇ | OCH₃ | C₂H₅ | 475 (M⁺) |
| 64 | 3-OPh | n-C₃H₇ | OCH₃ | C₂H₅ | 475 (M⁺) |
| 65 | 4-OPh(4-CH₃) | C₂H₅ | OCH₃ | C₂H₅ | 475 (M⁺) |
| 66 | 4-OPh(3-CH₃) | C₂H₅ | OCH₃ | C₂H₅ | 475 (M⁺) |
| 67 | 4-OPh(2-CH₃) | C₂H₅ | OCH₃ | C₂H₅ | 475 (M⁺) |
| 68 | 4-OPh(4-Cl) | C₂H₅ | OCH₃ | C₂H₅ | 495 (M⁺) |
| 69 | 4-OPh(3-Cl) | C₂H₅ | OCH₃ | C₂H₅ | 495 (M⁺) |
| 70 | 4-OPh(4-F) | C₂H₅ | OCH₃ | C₂H₅ | 479 (M⁺) |
| 71 | 4-OPh(4-Br) | C₂H₅ | OCH₃ | C₂H₅ | 539 (M⁺) |
| 72 | 4-OPh(4-OCH₃) | C₂H₅ | OCH₃ | C₂H₅ | 491 (M⁺) |
| 73 | 4-OPh(3-OCH₃) | C₂H₅ | OCH₃ | C₂H₅ | 491 (M⁺) |
| 74 | 4-OPh(2-OCH₃) | C₂H₅ | OCH₃ | C₂H₅ | 491 (M⁺) |
| 75 | 4-OPh(4-CH₃) | n-C₃H₇ | OCH₃ | C₂H₅ | 489 (M⁺) |
| 76 | 4-OPh(3-CH₃) | n-C₃H₇ | OCH₃ | C₂H₅ | 489 (M⁺) |
| 77 | 4-OPh(2-CH₃) | n-C₃H₇ | OCH₃ | C₂H₅ | 489 (M⁺) |
| 78 | 4-OPh(3-Cl) | n-C₃H₇ | OCH₃ | C₂H₅ | 509 (M⁺) |
| 79 | 4-OPh(4-OCH₃) | n-C₃H₇ | OCH₃ | C₂H₅ | 505 (M⁺) |
| 80 | 4-OPh(3-OCH₃) | n-C₃H₇ | OCH₃ | C₂H₅ | 505 (M⁺) |
| 81 | 4-OPh(2-OCH₃) | n-C₃H₇ | OCH₃ | C₂H₅ | 505 (M⁺) |
| 82 | 4-OPh(4-F) | n-C₃H₇ | OCH₃ | C₂H₅ | 493 (M⁺) |
| 83 | 4-OPh(4-Br) | n-C₃H₇ | OCH₃ | C₂H₅ | 553 (M⁺) |
| 84 | 4-OCF₃ | n-C₃H₇ | OCH₃ | C₂H₅ | 467 (M⁺) |
| 85 | 4-CH₃ | n-C₃H₇ | OCH₃ | C₂H₅ | 397 (M⁺) |
| 86 | 4-OCH₃ | n-C₃H₇ | OCH₃ | C₂H₅ | 413 (M⁺) |
| 87 | 4-Ph(4-Cl) | n-C₃H₇ | OCH₃ | C₂H₅ | 493 (M⁺) |
| 88 | 4-Ph(4-CH₃) | n-C₃H₇ | OCH₃ | C₂H₅ | 473 (M⁺) |
| 89 | 4-Ph(4-OCH₃) | n-C₃H₇ | OCH₃ | C₂H₅ | 489 (M⁺) |
| 90 | 4-OCH₂Ph(4-Cl) | n-C₃H₇ | OCH₃ | C₂H₅ | 523 (M⁺) |
| 91 | 4-OCH₂Ph(4-CH₃) | n-C₃H₇ | OCH₃ | C₂H₅ | 503 (M⁺) |
| 92 | 4-OPh(2-F) | n-C₃H₇ | OCH₃ | C₂H₅ | 493 (M⁺) |
| 93 | 4-OPh(2-OC₂H₅) | n-C₃H₇ | OCH₃ | C₂H₅ | 519 (M⁺) |
| 94 | 4-OPh(2-C₂H₅) | n-C₃H₇ | OCH₃ | C₂H₅ | 503 (M⁺) |

EXAMPLE 95 THROUGH 141

The compounds listed in Table 8 were obtained similarly to Example 20.

TABLE 8

$$\text{R}^1 \text{—} \underset{\text{benzyl-NH-C(=O)-Ar(R}^4\text{)-CH}_2\text{-CH(R}^2\text{)-COOH}}{\text{structure}}$$

| Example | R¹ | R² | R⁴ | Melting point (° C.) | Charac. formula | Elemental analysis (%) | |
|---|---|---|---|---|---|---|---|
| 95 | 4-CF$_3$ | n-C$_3$H$_7$ | OCH$_3$ | 147 | C$_{22}$H$_{24}$F$_3$NO$_4$ | Calcd.; | C 62.40, H 5.71, N 3.31 |
| | | | | | | Found; | C 62.33, H 5.65, N 3.39 |
| 96 | 4-OPh | n-C$_3$H$_7$ | OCH$_3$ | 117 | C$_{27}$H$_{29}$NO$_5$ | Calcd.; | C 72.46, H 6.53, N 3.13 |
| | | | | | | Found; | C 72.31, H 6.56, N 3.28 |
| 97 | 4-OCH$_2$Ph | n-C$_3$H$_7$ | OCH$_3$ | 111–112 | C$_{28}$H$_{31}$NO$_5$ | Calcd.; | C 72.86, H 6.77, N 3.03 |
| | | | | | | Found; | C 72.77, H 6.76, N 3.10 |
| 98 | 4-Ph | n-C$_3$H$_7$ | OCH$_3$ | 160–162 | C$_{27}$H$_{28}$NO$_4$.1/10H$_2$O | Calcd.; | C 74.84, H 6.79, N 3.23 |
| | | | | | | Found; | C 74.76, H 6.81, N 3.37 |
| 99 | 4-CF$_3$ | i-C$_3$H$_7$ | OCH$_3$ | 174–175 | C$_{22}$H$_{24}$F$_3$NO$_4$ | Calcd.; | C 62.40, H 5.71, N 3.31 |
| | | | | | | Found; | C 62.42, H 5.81, N 3.34 |
| 100 | 4-OPh | i-C$_3$H$_7$ | OCH$_3$ | 146–147 | C$_{27}$H$_{28}$NO$_5$ | Calcd.; | C 72.46, H 6.53, N 3.13 |
| | | | | | | Found; | C 72.43, H 6.60, N 3.15 |
| 101 | 4-OCH$_2$Ph | i-C$_3$H$_7$ | OCH$_3$ | 139–140 | C$_{28}$H$_{31}$NO$_5$ | Calcd.; | C 72.86, H 6.77, N 3.03 |
| | | | | | | Found; | C 72.75, H 6.75, N 3.07 |
| 102 | 4-Ph | i-C$_3$H$_7$ | OCH$_3$ | 157 | C$_{27}$H$_{28}$NO$_4$ | Calcd.; | C 75.15, H 6.77, N 3.25 |
| | | | | | | Found; | C 75.02, H 6.75, N 3.22 |
| 103 | 4-CF$_3$ | n-C$_4$H$_9$ | OCH$_3$ | 150 | C$_{23}$H$_{26}$F$_3$NO$_4$ | Calcd.; | C 63.15, H 5.99, N 3.20 |
| | | | | | | Found; | C 63.25, H 5.95, N 3.28 |
| 104 | 4-OPh | n-C$_4$H$_9$ | OCH$_3$ | 141–143 | C$_{28}$H$_{31}$NO$_5$ | Calcd.; | C 72.86, H 6.77, N 3.03 |
| | | | | | | Found; | C 72.69, H 6.82, N 3.05 |
| 105 | 4-OCH$_2$Ph | n-C$_4$H$_9$ | OCH$_3$ | 137–138 | C$_{29}$H$_{33}$NO$_5$.¹⁄₁₀H$_2$O | Calcd.; | C 72.96, H 7.01, N 2.93 |
| | | | | | | Found; | C 72.85, H 7.01, N 2.99 |
| 106 | 4-Ph | n-C$_4$H$_9$ | OCH$_3$ | 135–136 | C$_{28}$H$_{31}$NO$_4$ | Calcd.; | C 75.48, H 7.01, N 3.14 |
| | | | | | | Found; | C 75.33, H 7.02, N 3.23 |
| 107 | 4-OPh(4-CH$_3$) | C$_2$H$_5$ | OCH$_3$ | 126–127 | C$_{27}$H$_{29}$NO$_5$ | Calcd.; | C 72.46, H 6.53, N 3.13 |
| | | | | | | Found; | C 72.27, H 6.53, N 3.10 |
| 108 | 4-OPh(3-CH$_3$) | C$_2$H$_5$ | OCH$_3$ | 120–121 | C$_{27}$H$_{29}$NO$_5$ | Calcd.; | C 72.46, H 6.53, N 3.13 |
| | | | | | | Found; | C 72.47, H 6.48, N 3.10 |
| 109 | 4-OPh(2-CH$_3$) | C$_2$H$_5$ | OCH$_3$ | 142–143 | C$_{27}$H$_{29}$NO$_5$ | Calcd.; | C 72.46, H 6.53, N 3.13 |
| | | | | | | Found; | C 72.46, H 6.53, N 3.13 |
| 110 | 4-OPh(4-Cl) | C$_2$H$_5$ | OCH$_3$ | 143–144 | C$_{26}$H$_{26}$ClNO$_5$ | Calcd.; | C 66.73, H 5.60, N 2.99 |
| | | | | | | Found; | C 66.52, H 5.64, N 2.97 |
| 111 | 4-OPh(3-Cl) | C$_2$H$_5$ | OCH$_3$ | 131–132 | C$_{26}$H$_{26}$ClNO$_5$ | Calcd.; | C 66.73, H 5.60, N 2.99 |
| | | | | | | Found; | C 66.68, H 5.56, N 3.00 |
| 112 | 4-OPh(4-F) | C$_2$H$_5$ | OCH$_3$ | 137–139 | C$_{26}$H$_{26}$FNO$_5$ | Calcd.; | C 69.17, H 5.80, N 3.10 |
| | | | | | | Found; | C 69.09, H 5.85, N 3.12 |
| 113 | 4-OPh(4-Br) | C$_2$H$_5$ | OCH$_3$ | 148–149 | C$_{26}$H$_{26}$BrNO$_5$ | Calcd.; | C 60.95, H 5.11, N 2.73 |
| | | | | | | Found; | C 61.02, H 5.09, N 2.78 |
| 114 | 4-OPh(4-OCH$_3$) | C$_2$H$_5$ | OCH$_3$ | 124–125 | C$_{27}$H$_{29}$NO$_6$ | Calcd.; | C 69.96, H 6.31, N 3.02 |
| | | | | | | Found; | C 69.68, H 6.29, N 3.06 |
| 115 | 4-OPh(3-OCH$_3$) | C$_2$H$_5$ | OCH$_3$ | 112–113 | C$_{27}$H$_{29}$NO$_6$ | Calcd.; | C 69.96, H 6.31, N 3.02 |
| | | | | | | Found; | C 69.75, H 6.25, N 3.04 |
| 116 | 4-OPh(2-OCH$_3$) | C$_2$H$_5$ | OCH$_3$ | 124–125 | C$_{27}$H$_{29}$NO$_6$.¹⁄₁₀H$_2$O | Calcd.; | C 69.69, H 6.33, N 3.01 |
| | | | | | | Found; | C 69.53, H 6.32, N 2.93 |
| 117 | 4-OPh(4-CH$_3$) | n-C$_3$H$_7$ | OCH$_3$ | 139–141 | C$_{28}$H$_{31}$NO$_5$ | Calcd.; | C 72.86, H 6.77, N 3.03 |
| | | | | | | Found; | C 72.63, H 6.78, N 3.10 |
| 118 | 4-OPh(3-CH$_3$) | n-C$_3$H$_7$ | OCH$_3$ | 102–103 | C$_{29}$H$_{31}$NO$_6$.¹⁄₁₀H$_2$O | Calcd.; | C 72.58, H 6.79, N 3.02 |
| | | | | | | Found; | C 72.41, H 6.82, N 3.02 |
| 119 | 4-OPh(2-CH$_3$) | n-C$_3$H$_7$ | OCH$_3$ | 114 | C$_{28}$H$_{31}$NO$_5$ | Calcd.; | C 72.86, H 6.77, N 3.03 |
| | | | | | | Found; | C 72.83, H 6.83, N 3.12 |
| 120 | 4-OPh(3-Cl) | n-C$_3$H$_7$ | OCH$_3$ | 101–102 | C$_{27}$H$_{28}$ClNO$_5$ | Calcd.; | C 67.28, H 5.86, N 2.91 |
| | | | | | | Found; | C 67.23, H 5.80, N 2.90 |
| 121 | 4-OPh(4-OCH$_3$) | n-C$_3$H$_7$ | OCH$_3$ | 124–125 | C$_{28}$H$_{31}$NO$_6$ | Calcd.; | C 70.42, H 6.54, N 2.93 |
| | | | | | | Found; | C 70.36, H 6.57, N 2.99 |
| 122 | 4-OPh(3-OCH$_3$) | n-C$_3$H$_7$ | OCH$_3$ | 92–93 | C$_{28}$H$_{31}$NO$_6$ | Calcd.; | C 70.42, H 6.54, N 2.93 |
| | | | | | | Found; | C 70.13, H 6.64, N 2.87 |
| 123 | 4-OPh(2-OCH$_3$) | n-C$_3$H$_7$ | OCH$_3$ | 124–125 | C$_{28}$H$_{31}$NO$_6$.¹⁄₁₀H$_2$O | Calcd.; | C 70.16, H 6.56, N 2.92 |
| | | | | | | Found; | C 70.07, H 6.61, N 2.92 |
| 124 | 4-OPh(4-F) | n-C$_3$H$_7$ | OCH$_3$ | 148–149 | C$_{27}$H$_{28}$FNO$_6$ | Calcd.; | C 69.66, H 6.06, N 3.01 |
| | | | | | | Found; | C 69.36, H 6.06, N 3.02 |
| 125 | 4-OPh(4-Br) | n-C$_3$H$_7$ | OCH$_3$ | 153–154 | C$_{27}$H$_{27}$BrNO$_6$ | Calcd.; | C 61.60, H 5.36, N 2.66 |
| | | | | | | Found; | C 61.57, H 5.31, N 2.70 |
| 126 | 4-OCF$_3$ | n-C$_3$H$_7$ | OCH$_3$ | 126–127 | C$_{22}$H$_{24}$F$_3$NO$_6$ | Calcd.; | C 60.13, H 5.51, N 3.19 |
| | | | | | | Found; | C 59.86, H 5.50, N 3.16 |
| 127 | 4-CH$_3$ | n-C$_3$H$_7$ | OCH$_3$ | 115–116 | C$_{22}$H$_{27}$NO$_4$ | Calcd.; | C 71.52, H 7.37, N 3.79 |
| | | | | | | Found; | C 71.30, H 7.36, N 3.74 |
| 128 | 4-OCH$_3$ | n-C$_3$H$_7$ | OCH$_3$ | 149–150 | C$_{22}$H$_{27}$NO$_5$.¹⁄₁₀H$_2$O | Calcd.; | C 68.23, H 7.08, N 3.62 |
| | | | | | | Found; | C 68.21, H 7.10, N 3.60 |

TABLE 8-continued structure: R1-benzyl-NH-C(=O)- attached to benzene ring with R4, and -CH2-CH(R2)-COOH

| Example | R¹ | R² | R⁴ | Melting point (° C.) | Charac. formula | Elemental analysis (%) | |
|---|---|---|---|---|---|---|---|
| 129 | 4-Ph(4-Cl) | n-C₃H₇ | OCH₃ | 163–164 | C₂₇H₂₈ClNO₄ | Calcd.; | C 69.59, H 6.06, N 3.01 |
| | | | | | | Found; | C 69.55, H 6.03, N 3.03 |
| 130 | 4-Ph(4-CH₃) | n-C₃H₇ | OCH₃ | 155–156 | C₂₈H₃₁NO₄ | Calcd.; | C 75.48, H 7.01, N 3.14 |
| | | | | | | Found; | C 75.46, H 7.05, N 3.10 |
| 131 | 4-Ph(4-OCH₃) | n-C₃H₇ | OCH₃ | 146–147 | C₂₆H₃₁NO₆ | Calcd.; | C 72.86, H 6.77, N 3.03 |
| | | | | | | Found; | C 72.77, H 6.77, N 3.01 |
| 132 | 4-OCH₂Ph(4-Cl) | n-C₃H₇ | OCH₃ | 128–129 | C₂₉H₃₀ClNO₅ | Calcd.; | C 67.80, H 6.10, N 2.82 |
| | | | | | | Found; | C 67.78, H 6.05, N 2.85 |
| 133 | 4-OCH₂Ph(4-CH₃) | n-C₃H₇ | OCH₃ | 118–119 | C₂₉H₃₃NO₅ | Calcd.; | C 73.24, H 6.99, N 2.95 |
| | | | | | | Found; | C 73.11, H 6.90, N 2.96 |
| 134 | 4-CF₃ | C₂H₅ | OC₂H₅ | 119–120 | C₂₂H₂₄F₃NO₄ | Calcd.; | C 62.40, H 5.71, N 3.31 |
| | | | | | | Found; | C 62.33, H 5.70, N 3.32 |
| 135 | 2-OPh | C₂H₅ | OCH₃ | 146–147 | C₂₆H₂₇NO₆ | Calcd.; | C 72.04, H 6.28, N 3.23 |
| | | | | | | Found; | C 71.90, H 6.32, N 3.23 |
| 136 | 2-OPh | n-C₃H₇ | OCH₃ | 111–113 | C₂₇H₂₉NO₆ | Calcd.; | C 72.46, H 6.53, N 3.13 |
| | | | | | | Found; | C 72.53, H 6.49, N 3.11 |
| 137 | 3-OPh | C₂H₅ | OCH₃ | 91–92 | C₂₆H₂₇NO₆ | Calcd.; | C 72.04, H 6.28, N 3.23 |
| | | | | | | Found; | C 71.93, H 6.24, N 3.29 |
| 138 | 3-OPh | n-C₃H₇ | OCH₃ | 111–112 | C₂₇H₂₉NO₅ | Calcd.; | C 72.46, H 6.53, N 3.13 |
| | | | | | | Found; | C 72.40, H 6.59, N 3.17 |
| 139 | 4-OPh(2-F) | n-C₃H₇ | OCH₃ | 105–106 | C₂₇H₂₈FNO₅ | Calcd.; | C 69.66, H 6.06, N 3.01 |
| | | | | | | Found; | C 69.66, H 6.05, N 3.05 |
| 140 | 4-OPh(2-OC₂H₅) | n-C₃H₇ | OCH₃ | 121–123 | C₂₉H₃₂·¹⁄₁₀H₂O | Calcd.; | C 70.60, H 6.78, N 2.84 |
| | | | | | | Found; | C 70.33, H 6.78, N 2.84 |
| 141 | 4-OPh(2-C₂H₅) | n-C₃H₇ | OCH₃ | 113–115 | C₂₉H₃₃NO₅ | Calcd.; | C 73.24, H 6.99, N 2.95 |
| | | | | | | Found; | C 73.10, H 6.98, N 3.04 |

EXAMPLES 142 THROUGH 144

The compounds listed in Table 9 were obtained similarly to Example 42.

TABLE 9

| Example | R² | R³ | R⁴ | R⁵ | Mass analysis (m/z) |
|---|---|---|---|---|---|
| 142 | CH₃ | C₂H₅ | OCH₃ | C₂H₅ | 384 (M⁺) |
| 143 | C₂H₅ | C₂H₅ | OCH₃ | C₂H₅ | 398 (M⁺) |
| 144 | CH₂CF₃ | H | OCH₃ | C₂H₅ | 424 (M⁺) |

EXAMPLES 145 THROUGH 147

The compounds listed in Table 10 were obtained similarly to Example 43.

TABLE 10

| Example | R² | R³ | R⁴ | R⁵ | Mass analysis (m/z) |
|---|---|---|---|---|---|
| 145 | CH₃ | C₂H₅ | OCH₃ | C₂H₅ | 294 (M⁺) |
| 146 | C₂H₅ | C₂H₅ | OCH₃ | C₂H₅ | 308 (M⁺) |
| 147 | CH₂CF₃ | H | OCH₃ | C₂H₅ | 334 (M⁺) |

EXAMPLES 148 THROUGH 153

The compounds listed in Table 11 were obtained similarly to Example 44.

TABLE 11

| Example | R¹ | R² | R³ | R⁴ | R⁵ | Mass analysis (m/z) |
|---|---|---|---|---|---|---|
| 148 | 4-CF₃ | C₂H₅ | C₂H₅ | OCH₃ | C₂H₅ | 465 (M⁺) |

TABLE 11-continued

| Example | R¹ | R² | R³ | R⁴ | R⁵ | Mass analysis (m/z) |
|---|---|---|---|---|---|---|
| 149 | 4-OPh | $C_2H_5$ | $C_2H_5$ | $OCH_3$ | $C_2H_5$ | 489 (M⁺) |
| 150 | 4-$CF_3$ | $CH_3$ | $C_2H_5$ | $OCH_3$ | $C_2H_5$ | 451 (M⁺) |
| 151 | 4-OPh | $CH_3$ | $C_2H_5$ | $OCH_3$ | $C_2H_5$ | 475 (M⁺) |
| 152 | 4-$CF_3$ | $CH_2CF_3$ | H | $OCH_3$ | $C_2H_5$ | 491 (M⁺) |
| 153 | 4-OPh | $CH_2CF_3$ | H | $OCH_3$ | $C_2H_5$ | 515 (M⁺) |

EXAMPLES 154 THROUGH 159

The compounds listed in Table 12 were obtained similarly to Example 20.

TABLE 12

| Example | R¹ | R² | R³ | R⁴ | Melting point (° C.) | Charac. formula | | Elemental analysis (%) |
|---|---|---|---|---|---|---|---|---|
| 154 | 4-$CF_3$ | $C_2H_5$ | $C_2H_5$ | $OCH_3$ | 156–157 | $C_{23}H_{25}F_2NO_4$ | Calcd.; | C 63.15, H 5.99, N 3.20 |
| | | | | | | | Found; | C 63.04, H 5.93, N 3.16 |
| 155 | 4-OPh | $C_2H_5$ | $C_2H_5$ | $OCH_3$ | 144–145 | $C_{28}H_{31}NO_6 \cdot ¼H_2O$ | Calcd; | C 72.16, H 6.81, N 3.01 |
| | | | | | | | Found; | C 72.04, H 6.81, N 3.07 |
| 156 | 4-$CF_3$ | $CH_3$ | $C_2H_5$ | $OCH_3$ | 167–168 | $C_{22}H_{24}F_3NO_4$ | Calcd.; | C 62.40, H 5.71, N 3.31 |
| | | | | | | | Found; | C 62.33, H 5.78, N 3.30 |
| 157 | 4-OPh | $CH_3$ | $C_2H_5$ | $OCH_3$ | 142–143 | $C_{27}H_{29}NO_6$ | Calcd.; | C 72.46, H 6.53, N 3.13 |
| | | | | | | | Found; | C 72.38, H 6.43, N 3.09 |
| 158 | $CF_3$ | $CH_2CF_3$ | H | $OCH_3$ | 120–121 | $C_{21}H_{19}F_6NO_4$ | Calcd.; | C 54.43, H 4.13, N 3.02 |
| | | | | | | | Found; | C 54.37, H 4.19, N 3.07 |
| 159 | 4-OPh | $CH_2CF_3$ | H | $OCH_3$ | 119–120 | $C_{26}H_{24}F_3NO_6$ | Calcd.; | C 64.06, H 4.96, N 2.87 |
| | | | | | | | Found; | C 63.96, H 5.04, N 2.90 |

EXAMPLE 160

[3(2S),4S]-3-[2-ethyl-3-[4-methoxy-3-[N-[[4-(trifluoromethyl)phenyl]methyl]carbamoyl]phenyl] propionyl]-4-benzyloxazolidine-2-one (±)-2-Ethyl-3-[4-methoxy-3-[N-[[4-(trifluoromethyl) phenyl]-methyl]carbamoyl]phenyl]propanoic acid (Japanese Patent Application No. Hei 11-162235) (26.8 g, 65.6 mmol) and 34 ml of dehydrated tetrahydrofuran were mixed under an atmosphere of argon and triethylamine (9.14 ml, 65.8 mmol) and pivaloyl chloride (8.07 ml, 65.6 mmol) were added dropwise under stirring and cooling with ice, which was thereafter stirred for 1.5 hours at room temperature to synthesize the mixed acid anhydride derivative. On the other hand, in another vessel, potassium t-butoxide (8.83 g, 78.7 mmol) and 88 ml of dehydrated tetrahydrofuran were mixed under an atmosphere of argon and (S)-4-benzyloxazolidine-2-one (13.9 g, 78.7 mmol) dissolved into 70 ml of dehydrated tetrahydrofuran was added dropwise. After completion of the dropwise addition, the mixture was stirred for 45 minutes. Next, the suspension of the mixed acid anhydride derivative previously synthesized was added dropwise, while filtering under an atmosphere of argon. After completion of the dropwise addition, the reaction mixture was concentrated and then poured into water, which was extracted with ethyl acetate. The extract was washed with 5% hydrochloric acid, saturated sodium hydrogencarbonate and brine in sequence, then dried over anhydrous magnesium sulfate and concentrated. The residue was purified by silica gel chromatography (eluate n-hexane:ethyl acetate=3:2 v/v, then methylene chloride: methanol=15:1 v/v) to obtain 15.2 g (41%) of the diastereomer mixture. Diisopropyl ether and ether were added to this mixture, which was dissolved by heating, and then allowed to stand. The precipitated crystals were collected by filtration, washed with diisopropyl ether and then dried to obtain 5.62 g (15%) of the aimed compound as colorless crystals.

Mass analysis m/z 568(M⁺).

EXAMPLE 161

(S)-(+)-2-ethyl-3-[4-methoxy-3-[N-[[4-(trifluoromethyl)phenyl]methyl]carbamoyl]phenyl] propanoic acid

[3(2S),4S]-3-[2-ethyl-3-[4-methoxy-3-[N-[[4-(trifluoromethyl)phenyl]methyl]carbamoyl]phenyl] propionyl]-4-benzyloxazolidine-2-one (90.9 g, 0.160 mol) was dissolved into 802 ml of mixed solvent of tetrahydrofuran with water (4:1 v/v), which was cooled with ice under an atmosphere of argon. Under stirring, 30% aqueous hydrogen peroxide (63.7 ml, 0.630 mol) was added dropwise over 5 minutes. Following this, lithium hydroxide monohydrate (10.7 g, 0.256 mol) dissolved in 267 ml of water was added dropwise over 5 minutes and the mixture was stirred further for 1 hour under cooling with ice. 64% Sodium hydrogensulfite (102 g, 0.627 mol) dissolved in 401 ml of water was added dropwise to the reaction mixture. The reaction mixture was concentrated, the residue was poured into ice water, which was made acidic by adding 5% hydrochloric acid, and then extracted with methylene chloride. The extract was washed with brine, then dried over anhydrous magnesium sulfate and concentrated. The residue was dissolved in ethyl acetate and n-hexane by heating and allowed to stand. The precipitated crystals were collected by filtration and dried. Additionally, second crystals were obtained from the filtrate. The first crystals and the second crystals were combined, washed with mixed solvent of n-hexane with ethyl acetate (4:1 v/v) in suspended state, and then dried to obtain 52.4 g (80%) of the aimed compound as colorless crystalline powder.

Melting point 128–130° C.;

Mass analysis m/z 409(M$^+$);

Elemental analysis C$_{21}$H$_{22}$F$_3$NO$_4$ (409.40):

Calcd. C, 61.61; H, 5.42; N, 3.42.

Found C, 61.41; H, 5.44; N, 3.41.;

$^1$H-NMR (400 MHz, CDCl$_3$) δ0.95(3H,dd,J=7.3, 7.3 Hz), 1.54–1.70(2H, m), 2.58–2.65(1H,m), 2.77(1H,dd,J=13.7, 6.3 Hz), 2.96(1H,dd,J=13.7, 8.3 Hz), 3.92(3H,s), 4.38(1H, brs), 4.72(2H,d,J=5.9 Hz), 6.90(1H,d,J=8.3 Hz), 7.29 (1H, dd,J=8.3, 2.4 Hz), 7.46 (2H,d,J=7.8 Hz), 7.58(2H,d,J=7.8 Hz), 8.07(1H,d,J=2.4 Hz), 8.34(1H,t,J=5.9 Hz).

Specific rotation [α]$_D^{25}$+24°(C 0.8, MeOH);

Optical purity 99% e.e.(CHIRAL1 PAC AD 0.0046×0.25 m, eluate; n-hexane:isopropanol:trifluoroacetic acid= 80:20:0.2, detecting wave-length; 298 nm, column temperature; 30° C., flow rate; 1.00 ml/min).

EXAMPLE 162

(R)-3-(1-valeroyl)-4-benzyloxazolidine-2-one

Potassium t-butoxide (2.47 g, 22.0 mmol) and 50 ml of dehydrated tetrahydrofuran were mixed under an atmosphere of argon and (R)-4-benzyloxazolidine-2-one (3.55 g, 20.0 mmol) dissolved into 30 ml of dehydrated tetrahydrofuran was added dropwise under stirring and cooling with ice. After stirring for 30 minutes under cooling with ice, n-valeroyl chloride (2.60 ml, 21.9 mmol) dissolved in 20 ml of dehydrated tetrahydrofuran was added dropwise. After completion of the dropwise addition, the mixture was stirred for 1 hour and saturated aqueous solution of ammonium chloride was added to the reaction mixture, which was extracted with ethyl acetate. The extract was washed with water, saturated sodium hydrogencarbonate and brine in sequence, then dried over anhydrous sodium sulfate and concentrated. The residue was purified by silica gel chromatography (eluate n-hexane:ethyl acetate=4:1 v/v) to obtain 5.06 g (97%) of the aimed compound as a pale yellow oil.

Mass analysis m/z 261(M$^+$).

EXAMPLE 163

Benzyl 5-bromomethyl-2-methoxybenzoate

Benzyl 5-hydroxymethyl-2-methoxybenzoate (Patent Application No. Hei 11-162235) (15.5 g, 56.9 mmol) and 300 ml of dehydrated ether were mixed and phosphorus tribromide (2.0 ml, 21.1 mmol) was added dropwise under stirring and cooling with ice, which was further stirred for 1 hour. Ice water was added to the reaction mixture and ether layer was separated. The ether layer was washed with water, saturated sodium hydrogencarbonate and brine in sequence, then dried over anhydrous sodium sulfate and concentrated. The crystals obtained were recrystallized from diisopropyl ether to obtain 12.7 g (66%) of the aimed compound as colorless prisms.

Mass analysis m/z 334, 336(M$^+$).

EXAMPLE 164

[3(2S),4R]-3-[2-n-propyl-3-[4-methoxy-3-(benzyloxycarbonyl)phenyl]propionyl]-4-benzyloxazolidine-2-one (R)-3-(1-valeroyl)-4-benzyloxazolidine-2-one (3.56 g, 13.6 mmol) and 70 ml of dehydrated tetrahydrofuran were mixed under an atmosphere of argon, which was cooled to −78° C. Under stirring, 1 mol/l solution of sodium bis (trimethylsilyl)amide in tetrahydrofuran (15.0 ml, 15.0 mmol) was added dropwise. After completion of the dropwise addition, the mixture was stirred for 1 hour at −78° C. and then a solution of benzyl 5-bromomethyl-2-methoxybenzoate (5.04 g, 15.0 mmol) in tetrahydrofuran (20 ml) was added dropwise. After completion of the dropwise addition, the mixture was stirred for 3 hours at −78° C., followed by stirring for 3 hours at −35 to −40° C. Saturated aqueous solution of ammonium chloride was added to the reaction mixture, which was extracted with ethyl acetate. The extract was washed with water and brine in sequence, then dried over anhydrous sodium sulfate and concentrated. The residue was purified by silica gel chromatography (eluate n-hexane:ethyl acetate=4:1 v/v) to obtain 6.11 g (87%) of the aimed compound as a colorless oil.

Mass analysis m/z 515(M$^+$).

EXAMPLE 165

[3(2S),4R]-3-[2-ethyl-3-[4-methoxy-3-(benzyloxycarbonyl)phenyl]propionyl]-4-benzyloxazolidine-2-one Similarly to Example 5, the title compound was obtained as a colorless oil.

Mass analysis m/z 501(M$^+$).

EXAMPLE 166

[5(2S,4'R)]-2-methoxy-5-[[-2-(2-oxo-4-benzyloxazolidine-3-yl)carbonyl]pentyl]benzoic acid

[3(2S),4R]-3-[2-n-propyl-3-[4-methoxy-3-(benzyloxycarbonyl)phenyl]propionyl]-4-benzyloxazolidine-2-one (20.9 g, 40.5 mmol), 2.00 g of 10% palladium on activated carbon and 200 ml of ethyl acetate were mixed and catalytic hydrogenation was conducted at an initial hydrogen pressure of 294 kPa. After completion of the reaction, catalyst was filtered and washed with ethyl acetate. The reaction mixture and the washings were combined and concentrated to obtain 17.2 g (100%) of the aimed compound as a colorless oil.

Mass analysis m/z 425(M$^+$).

EXAMPLE 167

[5(2S,4'R)]-2-methoxy-5-[[2-(2-oxo-4-benzyloxazolidine-3-yl)-carbonyl]butyl]benzoic acid Similarly to Example 7, the title compound was obtained as a colorless oil.

Mass analysis m/z 411(M$^+$)

EXAMPLE 168

[3(2S),4R]-3-[2-n-propyl-3-[4-methoxy-3-[N-[(4-phenoxyphenyl)methyl]carbamoyl]phenyl]propionyl]-4-benzyloxazolidine-2-one

[5(2S,4'R)]-2-methoxy-5-[[2-(2-oxo-4-benzyloxazolidine-3-yl)carbonyl]pentyl]benzoic acid (12.1 g, 28.4 mmol), triethylamine (10.0 ml, 71.7 mmol) and 200 ml of dichloromethane were mixed and ethyl chlorocarbonate (3.05 ml, 31.3 mmol) was added dropwise under stirring and cooling with ice, After stirring for 20 minutes at 0° C., 4-phenoxybenzylamine hydrochloride (7.37 g, 31.3 mmol)

was added little by little. After stirring for 1 hour at 0° C., the mixture was stirred for 4 hours at room temperature. The reaction mixture was washed with 0.1 mol/l hydrochloric acid, water, saturated aqueous solution of sodium. hydrogencarbonate and brine in sequence, then dried over anhydrous sodium sulfate and concentrated. The residue was purified by silica gel chromatography (eluate n-hexane:ethyl acetate=7:3 v/v) to obtain 16.1 g (93%) of the aimed compound as a colorless oily product.

Mass analysis m/z 606($M^+$).

EXAMPLES 169 THROUGH 173

The compounds listed in Table 13 were obtained similarly to Example 168.

TABLE 13

| Example | $R^1$ | $R^2$ | $R^3$ | Mass analysis (m/z) |
|---------|-------|-------|-------|---------------------|
| 169 | 2-$OCH_3$ | $C_2H_5$ | $OCH_3$ | 622 ($M^+$) |
| 170 | 2-$OCH_3$ | n-$C_3H_7$ | $OCH_3$ | 636 ($M^+$) |
| 171 | 3-$OCH_3$ | n-$C_3H_7$ | $OCH_3$ | 636 ($M^+$) |
| 172 | 4-F | $C_2H_5$ | $OCH_3$ | 610 ($M^+$) |
| 173 | 4-F | n-$C_3H_7$ | $OCH_3$ | 624 ($M^+$) | was dissolved into 18 ml of mixed solvent of tetrahydrofuran with water (4:1 v/v), which was cooled with ice under an atmosphere of argon. Under stirring, 30% aqueous hydrogen peroxide (1.34 ml, 13.2 mmol) was added dropwise over 5 minutes. Following this, lithium hydroxide (222 mg, 5.30 mmol) dissolved in 6 ml of water was added dropwise over 5 minutes. The mixture was stirred further for 1 hour under cooling with ice. Sodium sulfite (1.37 g, 13.2 mmol) dissolved in 9 ml of water was added dropwise to the reaction mixture, which was stirred for 30 minutes as it was. The reaction mixture was poured into water, which was extracted with methylene chloride. The extract was washed with brine, then dried over anhydrous magnesium sulfate and concentrated. The residue was purified using diisopropyl ether:acetic acid=40:1 v/v to obtain 1.08 g (yield 73%) of aimed compound as colorless crystals.

Melting point 95–96° C.;
Mass analysis m/z 451($M^+$);
Elemental analysis C26H26FNO5 (451.49):
Calcd. C, 69.17; H, 5.80; N, 3.10.
Found C, 69.06; H, 5.73; N, 3.17.;
$^1$H-NMR (400 MHz, $CDCl_3$) δ0.95(3H,t,J=7.3 Hz), 1.54–1.69(2H,m), 2.60–2.65(1H,m), 2.75(1H,dd,J=13.7, 6.4 Hz), 2.96(1H,dd,J=13.7, 7.8 Hz), 3.89(3H,s), 4.63(2H,d,J= 5.9 Hz), 6.89–7.04(7H,m), 7.28–7.32(3H, m), 8.08(1H,d,J= 2.4 Hz), 8.24(1H,t,J=5.9 Hz).
Specific rotation $[\alpha]_D^{28}$+31°(C 0.8, MeCN);
Optical purity 97% e.e.(CHIRAL1 PAC OJ, 0.0046×0.25 m, eluate; n-hexane:isopropanol:trifluoroacetic acid= 90:10:0.1, detecting wave-length; 254 nm, column temperature; 40° C., flow rate; 1.00 ml/min).

EXAMPLES 175 THROUGH 179

The compounds listed in Table 14 were obtained similarly to Example 174.

TABLE 14

| Example | $R^1$ | $R^2$ | $R^3$ | Melting point (° C.) | Charac. formula | Elemental analysis (%) | | Angle of rotation ($[\alpha]_D$) | Optical purity (e.e.) |
|---------|-------|-------|-------|----------------------|-----------------|------------------------|---|----------------------------------|-----------------------|
| 175 | 2-$OCH_3$ | $C_2H_5$ | $OCH_3$ | 121–122 | $C_{27}H_{29}NO_5$ | Calcd.; | C 69.96, H 6.31, N 3.02 | +28° (C 0.57, MeCN) | 99% |
|     |     |     |     |     |     | Found; | C 69.77, H 6.28, N 3.09 |     |     |
| 176 | 2-$OCH_3$ | n-$C_3H_7$ | $OCH_3$ | 98–99 | $C_{28}H_{31}NO_6$ | Calcd.; | C 70.42, H 6.54, N 2.93 | +22° (C 0.50, MeCN) | 96% |
|     |     |     |     |     |     | Found; | C 70.34, H 6.60, N 3.10 |     |     |
| 177 | 3-$OCH_3$ | n-$C_3H_7$ | $OCH_3$ | 70–71 | $C_{28}H_{31}NO_6$ | Calcd.; | C 70.42, H 6.54, N 2.93 | +22° (C 0.53, MeCN) | 98% |
|     |     |     |     |     |     | Found; | C 70.52, H 6.54, N 3.06 |     |     |
| 178 | H | n-$C_3H_7$ | $OCH_3$ | 85–86 | $C_{27}H_{29}NO_5$ | Calcd.; | C 72.46, H 6.53, N 3.13 | +23° (C 0.54, MeCN) | 97% |
|     |     |     |     |     |     | Found; | C 72.42, H 6.54, N 3.19 |     |     |
| 179 | 4-F | n-$C_3H_7$ | $OCH_3$ | 126–127 | $C_{27}H_{29}FNO_5$ | Calcd.; | C 69.66, H 6.06, N 3.01 | +23° (C 0.52, MeCN) | 100% |
|     |     |     |     |     |     | Found; | C 69.55, H 6.07, N 3.06 |     |     |

EXAMPLE 174

(S)-(+)-2-ethyl-3-[4-methoxy-3-[N-[(4-fluorophenoxyphenyl)methyl]carbamoyl]phenyl] propanoic acid

[3(2S),4R]-3-[2-ethyl-3-[4-methoxy-3-[N-[(4-fluorophenoxyphenyl)methyl]carbamoyl]phenyl] propionyl]-4-benzyloxazolidine-2-one (2.02 g, 3.31 mol)

(The determination of optical purity is under the same conditions as Example 174 in Examples 177, 178 and 179, and, in Examples 175 and 176, mixed solvent of n-hexane: isopropanol:trifluoroacetic acid=85:15:0.1 was used for eluate and the others are same conditions as in Example 174).

EXAMPLES 180 THROUGH 188

The compounds listed in Table 15 were obtained similarly to Example 7.

TABLE 15

![Structure: R¹-(phenyl)-CH2-NH-C(=O)-(phenyl with R⁴)-CH2-CH(R²)-C(=O)-OR⁵]

| Example | R¹ | R² | R⁴ | R⁵ | Mass analysis (m/z) |
|---|---|---|---|---|---|
| 180 | 3-CF$_3$ | C$_2$H$_5$ | OCH$_3$ | C$_2$H$_5$ | 437 (M$^+$) |
| 181 | 4-OCF$_3$ | C$_2$H$_5$ | OCH$_3$ | C$_2$H$_5$ | 453 (M$^+$) |
| 182 | 2-OCH$_3$ | C$_2$H$_5$ | OCH$_3$ | C$_2$H$_5$ | 399 (M$^+$) |
| 183 | 3-OCH$_3$ | C$_2$H$_5$ | OCH$_3$ | C$_2$H$_5$ | 399 (M$^+$) |
| 184 | 4-OCH$_3$ | C$_2$H$_5$ | OCH$_3$ | C$_2$H$_5$ | 399 (M$^+$) |
| 185 | 4-OPh(4-OC$_2$H$_5$) | C$_2$H$_5$ | OCH$_3$ | C$_2$H$_5$ | 505 (M$^+$) |
| 186 | 4-OPh(4-OnC$_3$H$_7$) | C$_2$H$_5$ | OCH$_3$ | C$_2$H$_5$ | 399 (M$^+$) |
| 187 | 4-OPh(4-OC$_2$H$_5$) | nC$_3$H$_7$ | OCH$_3$ | C$_2$H$_5$ | 399 (M$^+$) |
| 188 | 4-OPh(4-OnC$_3$H$_7$) | nC$_3$H$_7$ | OCH$_3$ | C$_2$H$_5$ | 399 (M$^+$) |

EXAMPLES 189 THROUGH 197

The compounds listed in Table 16 were obtained similarly to Example 20.

TABLE 16

![Structure: R¹-(phenyl)-CH2-NH-C(=O)-(phenyl with R⁴)-CH2-CH(R²)-C(=O)-OH]

| Example | R¹ | R² | R⁴ | Melting point (° C.) | Charac. formula | | Elemental analysis (%) |
|---|---|---|---|---|---|---|---|
| 189 | 3-CF$_3$ | C$_2$H$_5$ | OCH$_3$ | 144–146 | C$_{21}$H$_{22}$F$_3$NO$_4$ | Calcd.; | C 60.72, H 5.50, N 3.37 |
|  |  |  |  |  |  | Found; | C 60.87, H 5.31, N 3.43 |
| 190 | 4-OCF$_3$ | C$_2$H$_6$ | OCH$_3$ | 135–137 | C$_{21}$H$_{22}$F$_3$NO$_6$ | Calc.; | C 59.29, H 5.21, N 3.29 |
|  |  |  |  |  |  | Found; | C 58.91, H 5.08, N 3.34 |
| 191 | 2-OCH$_3$ | C$_2$H$_5$ | OCH$_3$ | 120–121 | C$_{21}$H$_{25}$NO$_5$·¹⁄₁₀H$_2$O | Calcd.; | C 67.58, H 6.81, N 3.75 |
|  |  |  |  |  |  | Found; | C 67.32, H 6.74, N 3.73 |
| 192 | 3-OCH$_3$ | C$_2$H$_5$ | OCH$_3$ | 103–105 | C$_{21}$H$_{25}$NO$_6$·½H$_2$O | Calcd.; | C 66.30, H 6.89, N 3.68 |
|  |  |  |  |  |  | Found; | C 66.53, H 6.67, N 3.81 |
| 193 | 4-OCH$_3$ | C$_2$H$_6$ | OCH$_3$ | 143–144 | C$_{21}$H$_{26}$NO$_6$·⅓H$_2$O | Calcd.; | C 66.83, H 6.86, N 3.71 |
|  |  |  |  |  |  | Found; | C 66.85, H 6.69, N 3.76 |
| 194 | 4-OPh(4-OC$_2$H$_5$) | C$_2$H$_5$ | OCH$_3$ | 124–125 | C$_{28}$H$_{31}$NO$_6$ | Calcd.; | C 70.86, H 6.77, N 2.85 |
|  |  |  |  |  |  | Found; | C 70.69, H 6.71, N 2.89 |
| 195 | 4-OPh(4-OnC$_3$H$_7$) | C$_2$H$_5$ | OCH$_3$ | 114–116 | C$_{29}$H$_{33}$NO$_6$ | Calcd.; | C 71.27, H 6.98, N 2.77 |
|  |  |  |  |  |  | Found; | C 71.09, H 6.92, N 2.87 |
| 196 | 4-OPh(4-OC$_2$H$_5$) | n-C$_3$H$_7$ | OCH$_3$ | 123–125 | C$_{29}$H$_{33}$NO$_6$ | Calcd.; | C 71.27, H 6.98, N 2.77 |
|  |  |  |  |  |  | Found; | C 71.02, H 6.95, N 2.97 |
| 197 | 4-OPh(4-OnC$_3$H$_7$) | n-C$_3$H$_7$ | OCH$_3$ | 120–121 | C$_{30}$H$_{35}$NO$_6$ | Calcd.; | C 71.65, H 7.18, N 2.70 |
|  |  |  |  |  |  | Found; | C 71.35, H 7.17, N 2.85 |

[Biological Activity]

Test Example 1

Transactivation assay for human peroxisome proliferator-activated receptor (PPAR)α

To CHO cells cultured in a Dulbecco-modified Eagle's medium containing 10% delipidated fetal calf serum (FCS/DMEM), receptor plasmid that eXpresses fused protein of DNA-binding domain being transcription factor of yeast with ligand-binding domain of human type PPARα (Biochemistry, 1993, 32, 5598) its reporter plasmid (STRATAGENE Corp.), and luciferase plasmid of Renilla (Promega Corp.) as an internal standard were cotransfected with lipofectamine in the serum-free state. Thereafter, testing compound and (8S)-HETE being control compound were added to 10% FCS/DMEM and both luciferase activities were measured after 24 hours, which were corrected with internal standard.

Results are shown in Table 17. From these results, it was shown that the inventive compounds had potent transcriptional activity for human peroxisome proliferator-activated receptor α.

Test Example 2

Binding assay to human peroxisome proliferator-activated receptor (PPAR)α

A plasmid that eXpresses protein of human PPARα-ligand binding domain attached with histidine tag (His-hPPARα-LBD) was cultured by infecting to *Escherichia coli* (JM-109) and aimed protein was recovered and purified. [$^3$H]-5-[(2,4-dioxothiazolidine-5-yl)methyl]-2-methoxy-N-[[4-(trifluoromethyl)phenyl]methyl]benzamide (Amasham), testing compound and (8S)-HETE being control compound were incubated for 45 minutes at room temperature at various concentrations together with His-hPPARα-LBD protein in 10 mmol/l Tris hydrochloride buffer (pH 7.4) containing 50 mmol/l potassium chloride and 10 mmol/l dithiothreitol. After the reaction, amount of [$^3$H]-5-[(2,4-dioxothiazolidine-5-yl)methyl]-2-methoxy-N-[[4-(trifluoromethyl)phenyl]methyl]benzamide was determined by a liquid scintillation counter.

Results are shown in Table 17. From these results, it was shown that the inventive compounds had potent binding activity to human peroxisome proliferator-activated receptor α.

TABLE 17

| Example | Transcriptional activity EC$_{50}$(μmol/l) | Binding activity EC$_{50}$(μmol/l) |
| --- | --- | --- |
| 20 | 0.0115 | 0.19 |
| 22 | 0.11 | 0.43 |
| 23 | 0.024 | 0.74 |
| 24 | 0.18 | 0.56 |
| 30 | 0.20 | 0.84 |
| (8S) HETE | 1.30 | 0.17 |

Test Example 3
Test on Lipid-lowering Action

After SD strain male rats (Nippon Charles Liver) were bred from 8-(weeks old) with feed (Nippon Clear), test was started from 11-(weeks old). After (fasting) for 2 days, testing compound and Bezafibrate (30 mg/kg), being control compound, suspended into 0.5% solution of arabic gum were administered orally once a day for continuous 4 days. For the feed during administration period, AIN-93M modified fructose-loaded diet (Oriental Yeast) was used. After administration for 4 days, blood was collected from (trial) vein and the blood levels of triglyceride, total cholesterol, and free fatty acid were determined by enzymatic method.

The lowering rate of triglyceride in blood, overall cholesterol and free fatty acid was calculated, respectively, by determining the proportion of a figure obtained by subtracting average level of triglyceride in blood (or, average level of (total) cholesterol or level of free fatty acid) of dosage group from average level of triglyceride in blood (or, average level of (total) cholesterol or level of free fatty acid) of vehicle control group to average level of triglyceride in blood (or, average level of overall cholesterol or level of free fatty acid) of vehicle control group.

Results are shown in Table 18. As evident from these results, it was shown that the inventive compounds had excellent blood lipids (cholesterol and neutral lipid)lowering action.

TABLE 18

| Example | Dosage (mg/kg) | Lowering rate (%) | | |
| --- | --- | --- | --- | --- |
| | | Free fatty acid | Total cholesterol | Triglyceride in blood |
| 20 | 10 | 77 | 25 | 53 |
| 20 | 30 | 53 | 55 | 56 |
| Bezafibrate | 30 | 37 | 49 | 64 |

Test Example 4

Test of transcription activation on human peroxisome proliferator-activated receptor (PPAR)α

The test of transcription activation on human peroxisome proliferator-activated receptor (PPAR)α shown in Test example 1 was performed to obtain results shown in Table 19.

TABLE 19

| Example | Transcriptional activity EC$_{50}$ (μmol/l) |
| --- | --- |
| 174 | 0.024 |
| 178 | 0.094 |

TABLE 19-continued

| Example | Transcriptional activity EC$_{50}$ (μmol/l) |
| --- | --- |
| 179 | 0.0092 |

From these results, it was shown that the inventive compounds had potent transcriptional activity for human peroxisome proliferator-activated receptor α.

[Result]

From the results as described above, the inventive substituted phenylpropanonic acid derivatives are novel compounds group with excellent binding activity to human PPARα, transcriptional activity, and blood lipids (cholesterol and neutral lipid)-lowering action.

With these inventive compounds, from the fact that they have agonistic activity on human PPARα, it can be said that they are effective compounds as lipid-lowering drugs aforementioned, in particular, lipid-lowering drugs for liver, and suppressing drugs for the progress of arteriosclerosis.

What is claimed is:

1. A compound represented by formula (1), a pharmaceutically salt thereof or a hydrate thereof:

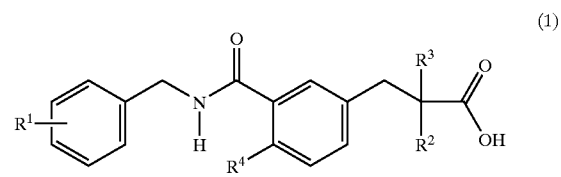

(1)

wherein R$^1$ is a lower alkyl group with 1 to 4 carbon atoms, a lower alkoxy group with 1 to 3 carbon atoms, a trifluoromethyl group, a trifluoromethoxy group, a substituted phenyl group, an unsubstituted phenyl group, a substituted phenoxy group, an unsubstituted phenoxy group, a substituted benzyloxy group, or an unsubstituted bezyloxy group;

R$^2$ is a lower alkyl group with 1 to 4 carbon atoms, a 2,2,2-trifluoroethyl group, a lower alkoxy group with 1 to 3 carbon atoms, a phenoxy group, a lower alkylthio group with 1 to 3 carbon atoms, a phenylthio group, or a benzylthio group, wherein if R$^2$ is a lower alkyl group with 1 to 4 carbon atoms, or a 2,2,2-trifluoroethyl group then R$^3$ is a hydrogen atom, or lower alkyl group with 1 to 4 carbon atoms; and if R$^2$ is a lower alkoxy group with 1 to 3 carbon atoms, a phenoxy group, a lower alkylthio group with 1 to 3 carbon atoms, a phenylthio group, or a benzylthio group then R$^3$ is a hydrogen atom; and R$^4$ is a lower alkoxy group with 1 to 3 carbon atoms.

2. The compound, the pharmaceutically acceptable salt thereof, or the hydrate thereof according to claim 1, which has the steric configuration represented in formula (1a):

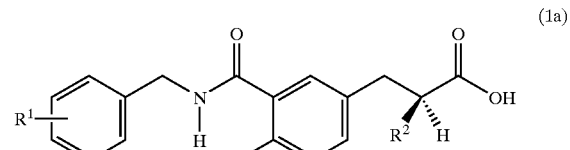

(1a)

wherein R$^1$ is a lower alkyl group with 1 to 4 carbon atoms, a lower alkoxy group with 1 to 3 carbon atoms, a trifluoromethyl group, a trifluoromethoxy group, a substituted phenyl group, an unsubstituted phenyl group, a substituted phenoxy group, an unsubstituted phenoxy group, a substituted benzyloxy group, or an unsubstituted benzyloxy group;

$R^2$ is a lower alkyl group with 1 to 4 carbon atoms, a 2,2,2-trifluoroethyl group, a lower alkoxy group with 1 to 3 carbon atoms, a lower alkylthio group with 1 to 3 carbon atoms, a phenylthio group, or benzylthio group; and $R^4$ is a lower alkoxy group with 1 to 3 carbon atoms.

3. The compound, the pharmaceutically acceptable salt thereof, or the hydrate thereof according to claim 1, wherein $R^1$ is a trifluoromethyl group.

4. The compound, the pharmaceutically acceptable salt thereof, or the hydrate thereof according to claim 1, wherein $R^1$ is a benzyloxy group.

5. The compound, the pharmaceutically acceptable salt thereof, or the hydrate thereof according to claim 1, wherein $R^1$ is a phenoxy group.

6. The compound, the pharmaceutically acceptable salt thereof, or the hydrate thereof according to claim 1, wherein $R^2$ is an ethyl group.

7. The compound, the pharmaceutically acceptable salt thereof, or the hydrate thereof according to claim 1, wherein $R^2$ is a methoxy group.

8. The compound, the pharmaceutically acceptable salt thereof, or the hydrate thereof according to claim 1, wherein $R^2$ is an n-propyl group.

9. The compound according to claim 1, which is 2-methoxy-3-[4-methoxy-3-[N-[[4-(trifluoromethyl)phenyl]methyl]carbamoyl]phenyl]propanonic acid, a pharmaceutically acceptable salt, or a hydrate thereof.

10. The compound according to claim 1, which is 2-ethyl-3-[4-methoxy-3-[N-[[4-(trifluoromethyl)phenyl]methyl]carbamoyl]phenyl]propanoic acid, a pharmaceutically acceptable salt thereof, or a hydrate thereof.

11. The compound according to claim 1, which is 2-n-propyl-3-[4-methoxy-3-[N-[[4-(phenoxy)phenyl]methyl]carbamoyl]phenyl]propanoic acid, a pharmaceutically acceptable salt thereof, or a hydrate thereof.

12. The compound according to claim 1, which is (+)-2-ethyl-3-[4-methoxy-3-[N-[[4-(trifluoromethyl)phenyl]methyl]carbamoyl]phenyl]propanonic acid, a pharmaceutically acceptable salt thereof, or a hydrate thereof.

13. The compound, the pharmaceutically acceptable salt thereof, or the hydrate thereof according to claim 1, wherein $R^1$ is a 3-methoxyphenoxy group.

14. The compound, the pharmaceutically acceptable salt thereof, or the hydrate thereof according to claim 1, wherein $R^1$ is a 4-fluorophenoxy group.

15. The compound, the pharmaceutically acceptable salt thereof, or the hydrate thereof according to claim 1, wherein $R^1$ is a 2-methoxyphenoxy group.

16. The compound according to claim 1, which is 2-ethyl-3-[4-methoxy-3-[N-[[4-(2-methoxyphenoxy)phenyl]methyl]carbamoyl]phenyl]propanoic acid, a pharmaceutically acceptable salt thereof, or a hydrate thereof.

17. The compound according to claim 1, which is 2-n-propyl-3-[4-methoxy-3-[N-[[4-(2-methoxyphenoxy)phenyl]methyl]carbamoyl]phenyl]propanoic acid, a pharmaceutically acceptable salt thereof, or a hydrate thereof.

18. The compound according to claim 1, which is 2-ethyl-3-[4-methoxy-3-[N-[[4-(3-methoxyphenoxy)phenyl]methyl]carbamoyl]phenyl]propanoic acid, a pharmaceutically acceptable salt thereof, or a hydrate thereof.

19. The compound according to claim 1, which is 2-n-propyl-3-[4-methoxy-3-[N-[[4-(3-methoxyphenoxy)phenyl]methyl]carbamoyl]phenyl]propanoic acid, a pharmaceutically acceptable salt thereof, or a hydrate thereof.

20. The compound according to claim 1, which is 2-ethyl-3-[4-methoxy-3-[N-[[4-(4-fluorophenoxy)phenyl]methyl]carbamoyl]phenyl]propanoic acid, a pharmaceutically acceptable salt thereof, or a hydrate thereof.

21. A compound according to claim 1, which is 2-n-propyl-3-[4-methoxy-3-[N-[[4-(4-fluorophenoxy)phenyl]methyl]carbamoyl]phenyl]propanoic acid, a pharmaceutically acceptable salt thereof, or a hydrate thereof.

22. The compound according to claim 1, which is (S)-2-ethyl-3-[4-methoxy-3-[N-[[4-(trifluoromethyl)phenyl]methyl]carbamoyl]phenyl]propanoic acid, a pharmaceutically acceptable salt thereof, or a hydrate thereof.

23. The compound according to claim 1, which is (S)-2-ethyl-3-[4-methoxy-3-[N-[(4-phenoxyphenyl)methyl]carbamoyl]phenyl]propanoic acid, a pharmaceutically acceptable salt thereof, or a hydrate thereof.

24. The compound according to claim 1, which is (S)-2-ethyl-3-[4-methoxy-3-[N-[[4-(2-methoxyphenoxy)phenyl]methyl]carbamoyl]phenyl]propanoic acid, a pharmaceutically acceptable salt thereof, or a hydrate thereof.

25. The compound according to claim 1, which is (S)-2-ethyl-3-[4-methoxy-3-[N-[[4-(4-fluorophenoxy)phenyl]methyl]carbamoyl]phenyl]propanoic acid, a pharmaceutically acceptable salt thereof, or a hydrate thereof.

26. The compound according to claim 1, which is (S)-n-propyl-3-[4-methoxy-3-[N-[(4-phenoxyphenyl)methyl]carbamoyl]phenyl]propanoic acid, a pharmaceutically acceptable salt thereof, or a hydrate thereof.

27. The compound according to claim 1, which is (S)-n-propyl-3-[4-methoxy-3-[N-[[4-(2-methoxyphenoxy)phenyl]methyl]carbamoyl]phenyl]propanoic acid, a pharmaceutically acceptable salt thereof, or a hydrate thereof.

28. The compound according to claim 1, which is (S)-n-propyl-3-[4-methoxy-3-[N-[[4-(3-methoxyphenoxy)phenyl]methyl]carbamoyl]phenyl]propanoic acid, a pharmaceutically acceptable salt thereof, or a hydrate thereof.

29. The compound according to claim 1, which is (S)-2-n-propyl-3-[4-methoxy-3-[N-[[4-(4-fluorophenoxy)phenyl]methyl]carbamoyl]phenyl]-propanoic acid, a pharmaceutically acceptable salt thereof, or a hydrate thereof.

30. The compound according to claim 1, which is 2-Ethyl-3[4-methoxy-3-[N-[[4-(trifluoromethyoxy)phenyl]methyl]carbamoyl]phenyl]propanoic acid, a pharmaceutically acceptable salt thereof, or a hydrate thereof.

31. The compound according to claim 1, which is (S)-(+)-2-Ethyl-3-[4-methoxy-3-[N-[[4-(trifloromethoxy)phenyl]methyl]carbamoyl]phenyl]-propanoic acid, a pharmaceutically acceptable salt thereof, or a hydrate thereof.

32. A composition comprising one or more compounds represented by formula (1), pharmaceutically acceptable salts thereof, or hydrates thereof as effective ingredients:

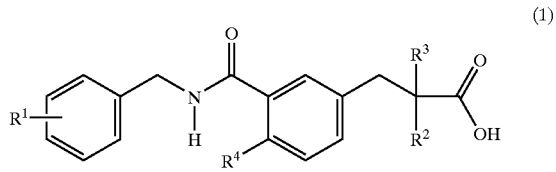

(1)

wherein $R^1$ is a lower alkyl group with 1 to 4 carbon atoms, a lower alkoxy group with 1 to 3 carbon atoms, a trifluoromethyl group, a trifluoromethoxy group, a substituted phenyl group, an unsubstituted phenyl group, a substituted phenoxy group, an unsubstituted phenoxy group, a substituted benzyloxy group, or an unsubstituted bezyloxy group;

$R^2$ is a lower alkyl group with 1 to 4 carbon atoms, a 2,2,2-trifluoroethyl group, a lower alkoxy group with 1 to 3 carbon atoms, a phenoxy group, a lower alkylthio group with 1 to 3 carbon atoms, a phenylthio group, or a benzylthio group, wherein if $R^2$ is a lower alkyl group with 1 to 4 carbon atoms, or a 2,2,2-trifluoroethyl group then $R^3$ is a hydrogen atom, or lower alkyl group with 1 to 4 carbon atoms; and if $R^2$ is a lower alkoxy group with 1 to 3 carbon atoms, a phenoxy group, a lower alkylthio group with 1 to 3 carbon atoms, a phenylthio group, or a benzylthio group then $R^3$ is a hydrogen atom; and $R^4$ is a lower alkoxy group with 1 to 3 carbon atoms; and a carrier.

33. The composition of claim 32 which is a lipid-decreasing drug.

34. The composition according to claim 32, which is a human peroxisome proliferant-activated receptor (PPAR)α agonist.

35. The composition according to claim 32, which is a therapeutic drug for arteriosclerosis.

36. A composition comprising one or more compounds, pharmaceutically acceptable salts thereof, or hydrates thereof according to claim 2, as effective ingredients; and a carrier.

37. The composition according to claim 36, which is a lipid-decreasing drug.

38. The composition according to claim 36, which is a human peroxisome proliferant-activated receptor (PPAR)α agonist.

39. The composition according to claim 36, which is a therapeutic drug for arteriosclerosis.

40. A process for preparing a compound represented by formula (1a)

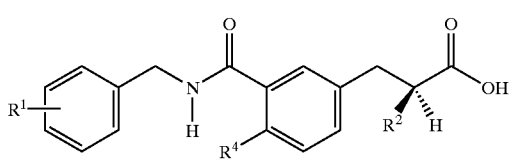

(1a)

comprising reacting compound represented by formula (1e)

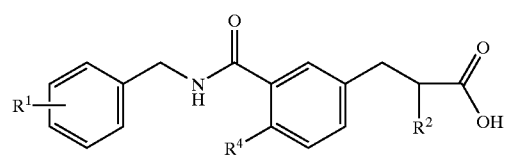

(1e)

with pivaloyl chloride to obtain a compound represented by formula (23)

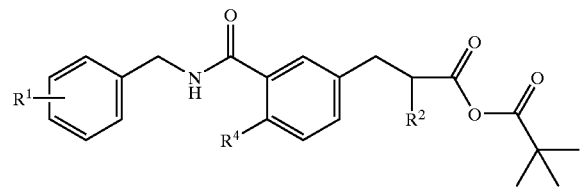

(23)

reacting a compound represented by formula (23) with a compound represented by formula (24)

$$Xp'—H \quad (24)$$

to obtain a compound represented by formula (25)

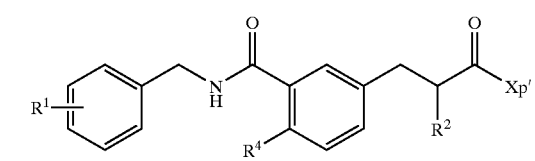

(25)

separating each diastereomer of the compound of formula (25) by recrystallization or column chromatography to obtain a compound represented by formula (26)

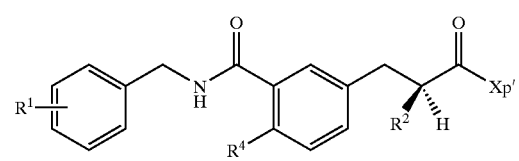

(26)

and hydrolyzing the Xp' substituent in the compound of formula (26);

wherein $R^1$ is a lower alkyl group with 1 to 4 carbon atoms, a lower alkoxy group with 1 to 3 carbon atoms, a trifluoromethoxy group, a substituted phenyl group, an unsubstituted phenyl group, a substituted phenoxy group, an unsubstituted phenoxy group, a substituted benzyloxy group, or an unsubstituted benzyloxy group;

$R^2$ is a lower alkyl group with 1 to 4 carbon atoms, a 2,2,2-trifluoroethyl group, a lower alkoxy group with 1 to 3 carbon atoms, a phenoxy group, a lower alkylthio group with 1 to 3 carbon atoms, a phenylthio group, or a benzylthio group;

$R^4$ is a lower alkoxy group with 1 to 3 carbon atoms; and

Xp' is an optically active chiral oxazolodinone.

41. The process according to claim 40, wherein the optically active chiral oxazolidinone is selected from the group consisting of 4-benzyl-2-oxazolidinone-3-yl group, 4-isopropyl-2-oxazolidinone-3-yl group or 4-phenyl-2-oxazolidinone-3-yl group, chiral imidazolidinone, chiral cyclic lactam, and chiral sultam.

42. A process for preparing a compound represented by formula (1a)

(1a)

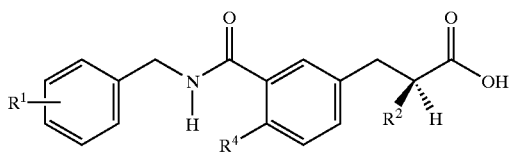

comprising reacting a compound represented by formula (27)

(27)

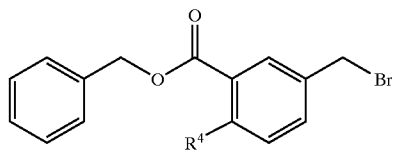

with a compound represented by formula (30)

(30)

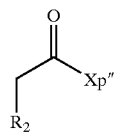

to obtain compounds represented by formula (28)

(28)

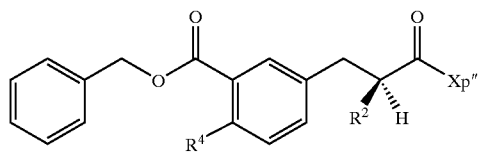

hydrogenolyzing the compound of formula (28) to obtain a compound represented by formula (29)

(29)

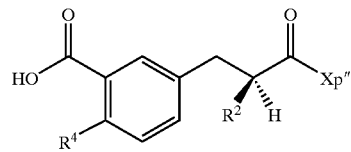

reacting a compound of formula (29) with a compound represented by formula (7)

(7)

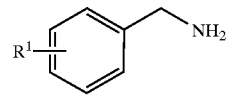

to obtain compounds represented by formula (26a)

(26a)

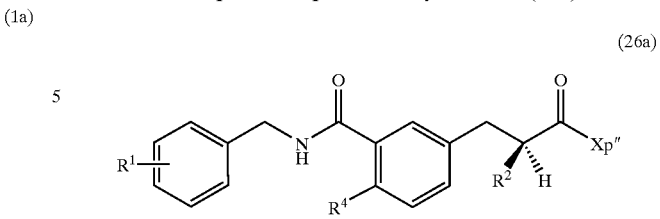

and hydrolyzing the Xp" substitutent in the compound of formula (26a)

wherein $R^1$ is a lower alkyl group with 1 to 4 carbon atoms, a lower alkoxy group with 1 to 3 carbon atoms, a trifluoromethyl group, a trifluoromethoxy group, a substituted phenyl group, an unsubstituted phenyl group, a substituted phenoxy group, an unsubstituted phenoxy group, a substituted benzyloxy group, or an unsubstituted benzyloxy group;

$R^2$ is a lower alkyl group with 1 to 4 carbon atoms, a lower alkoxy group with 1 to 3 carbon atoms, a phenoxy group, a lower alkylthio group with 1 to 3 carbon atoms, a phenylthio group, or a benzylthio group;

$R^4$ is a lower alkoxy group with 1 to 3 carbon atoms of 1 to 3; and

Xp" is a chiral oxazolidinone with an absolute configuration of (R).

43. The process as claimed in claim 42, wherein Xp" is selected from the group consisting of (R)-4-benzyl-2-oxazolidinone-3-yl group, (R)-4-isopropyl-2-oxazolidinone-3-yl group or (R)-4-phenyl-2-oxazolidinone-3-yl group, chiral imidazolidinone, chiral cyclic lactam, and chiral sultam.

44. A method of lowering lipid levels in the blood of a subject, comprising administering the composition of claim 32 to said subject in an amount sufficient to lower the lipid levels in the blood relative to the lipid levels in the blood prior to said administering.

45. A method of lowering lipid levels in the blood of a subject, comprising administering the composition of claim 36 to said subject in an amount sufficient to lower the lipid levels in the blood relative to the lipid levels in the blood prior to said administering.

46. A method of transactivating a human peroxisome proliferant-activated receptorα in a cell, comprising administering the composition of claim 32 to said cell in an amount sufficient to transactivate the human peroxisome proliferant-activated receptorα in the cell.

47. A method of transactivating a human peroxisome proliferant-activated receptorα in a cell, comprising administering the composition of claim 36 to said cell in an amount sufficient to transactivate the human peroxisome proliferant-activated receptorα in the cell.

* * * * *